(12) United States Patent
Prosl et al.

(10) Patent No.: US 6,350,251 B1
(45) Date of Patent: Feb. 26, 2002

(54) BIOCIDAL LOCKS

(75) Inventors: Frank R. Prosl, Duxbury; Brian K. Estabrook, Middleboro, both of MA (US); Klaus Sodemann, Lahr (DE)

(73) Assignee: Biolink Corporation, Norwell, MA (US)

( * ) Notice: Subject to any disclaimer, the term of this patent is extended or adjusted under 35 U.S.C. 154(b) by 0 days.

(21) Appl. No.: 09/483,966

(22) Filed: Jan. 18, 2000

(51) Int. Cl.[7] .............................................. A61M 11/00
(52) U.S. Cl. ...................... 604/93; 514/222.5
(58) Field of Search ........................ 604/93, 8, 9, 94, 604/95; 514/222.5, 223.5

(56) References Cited

U.S. PATENT DOCUMENTS 5,077,281 A  * 12/1991  Ruinmüller ................. 514/56
5,210,083 A  *  5/1993  Pfirrmann ................. 514/222.5
6,166,007 A  * 12/2000  Sodenenn ................. 514/222.5

* cited by examiner

*Primary Examiner*—Michael A. Brown
(74) *Attorney, Agent, or Firm*—Frederick C. Williams; Williams & Associates

(57) ABSTRACT

Disclosed herein is an internal prosthetic device comprising:
(a) device for providing a continuous flowpath, crossing a patient's skin, between an external-to-patient site and an internal-to-patient site;
(b) means for blocking the flowpath; and
(c) a biocidal lock including:
  (i) an anticoagulant; and
  (ii) a non-antibiotic biocide.

78 Claims, 8 Drawing Sheets

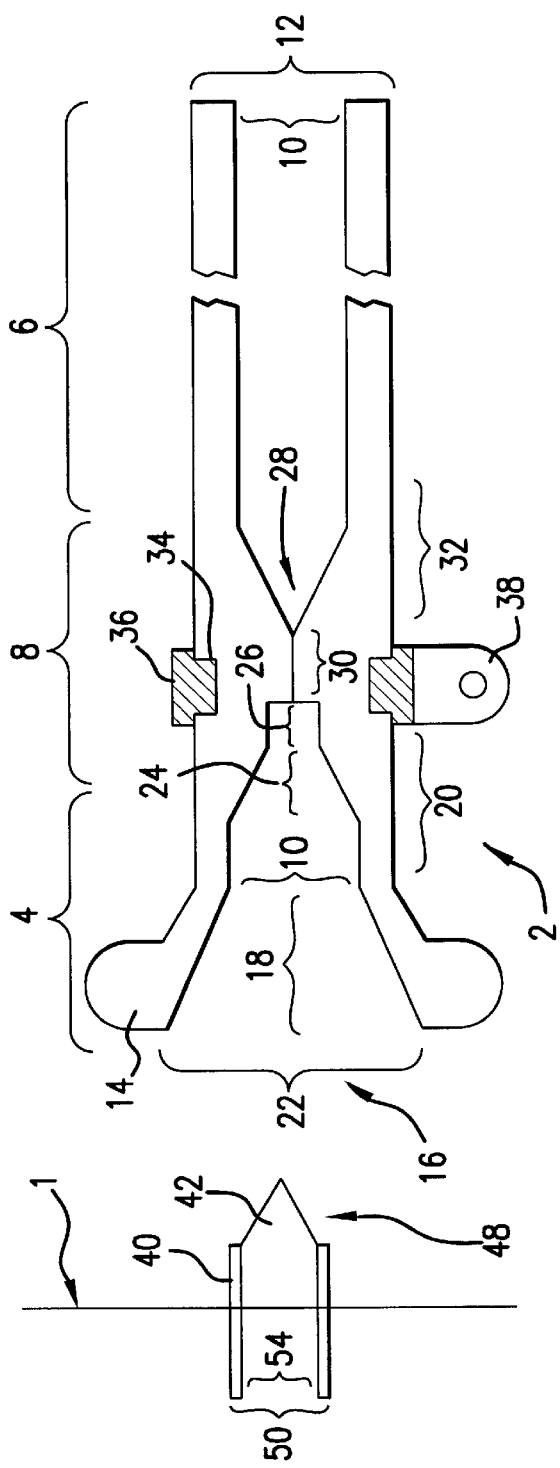
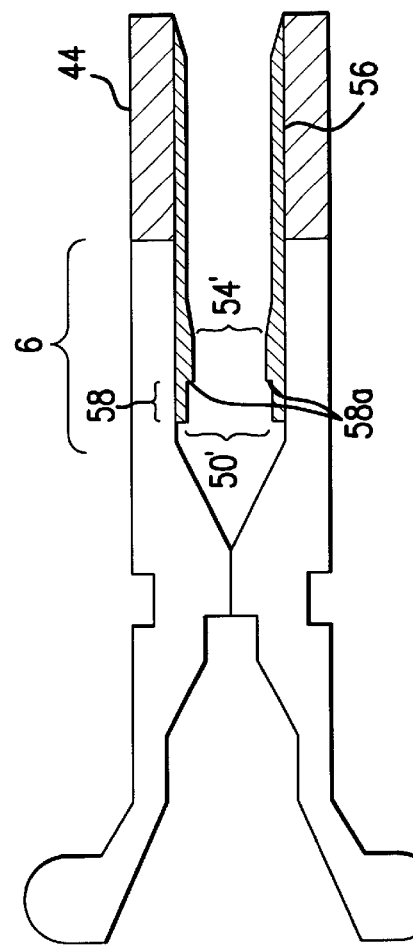
FIG.1
FIG.2

BIOCIDAL LOCKS

BACKGROUND OF THE INVENTION

1. Field of the Invention

The present invention relates to prosthetic devices for use internally in a patient (hereinafter "internal prosthetic devices"), especially catheters and ports, and to compositions and methods for their flushing and coating to prevent infection and blood coagulation. In accordance with the present invention, biocidal/anti-coagulant compositions are provided for use in flushing and coating internal prosthetic devices, especially ports and catheters.

2. Description of Related Art

Hemodialysis access systems for access to a human or animal patient's vascular system for exchange of blood between the vascular system and an external processing apparatus are well known in the art. One method comprises a catheter placed in the patient with one end extending into the central venous system and the other end affixed to one of several possible devices placed within the patient's body that are generally referred to as "ports." Herein, "vessel" is defined as any conduit carrying a fluid within the patient's body. These devices generally comprise a chamber having an access opening sealed by means of a septum and having an egress from a second location leading to the catheter that is disposed within a fluid space or vessel. The septum allows a needle to pass into the chamber, but then closes when the needle is removed, thereby preventing leakage from within the space or vessel and also preventing anything from entering or exiting the chamber. These devices are usually implanted below the skin to prevent infection, other contamination, and mishandling.

Recently, an improved device of this class has been developed and described in U.S. Pat. No. 5,954,691 and U.S. patent application Ser. No. 09/083,078, filed May 21, 1998. These inventions are directed to a hemodialysis access system for access to a human or animal patient's vascular system for high fluid flow rate exchange of blood between the vascular system and an external processing apparatus at a volumetric flow rate in excess of 250 mL/minute, and comprising, in combination, (a) a needle assembly comprising a lumen defined by an interior surface and constructed and arranged for puncturing the skin of the patient and for carrying blood therethrough at a flow rate consistent with the high blood flow requirement of the blood exchange process;

(b) a subcutaneously implantable access device permitting fluid connection to a vessel or space within a patient's body, the device comprising (i) a channel structure providing a flowpath having a straight or gently changing flow direction and having an interior surface and a distal end and a proximal end with reference to the patient's skin puncture site and constructed and arranged for insertion of the needle through the proximal end of the channel and withdrawal of the needle therefrom, (ii) a seal arranged within the channel and movable between first and second positions, where the seal, in the first position, with the needle not inserted through the seal, prevents fluids from passing the seal and, in the second position, with the needle inserted through the seal, allows fluids to pass through the needle and emerge substantially at the channel distal end, and where blood flowpath transitions between the needle interior surface and the channel interior surface are substantially continuous and smooth when the means for sealing is in the second position; and the device further comprising structure for joining the channel distal end to a catheter that extends to an internal vessel of the patient's body, and wherein such joining is continuous and smooth along the interior surfaces of the channel and catheter.

As with any invasive procedure, prevention of infection has been a problem, particularly with a device that must remain in place over protracted periods of time. Coagulation of the blood in and around the catheter and/or port has also proven troublesome and methods are needed for its prevention, particularly with regard to inhibiting the clogging of the catheter, which can diminish or destroy its usefulness. A significant amount of research has been directed to the alleviation of these problems.

It is standard procedure to flush catheters and/or ports with an anticoagulant, such as heparin. However, heparin is not an antibacterial and, in addition, if not carefully controlled, it can carry the anti-coagulation process too far, thereby presenting a risk of hemorrhage. It is also known in the art to employ an antibiotic along with the anticoagulant, but if this is done, as is always the case with the use of antibiotics, the probability increases that hybrid microorganisms will be produced having immunity to the applied antibiotic. For this reason, it is desirable in the medical arts to minimize the use of antibiotics to as great an extent as possible in order to conserve their efficacy over a prolonged period.

U.S. Pat. No. 4,107,305 discloses a method of combating endotoxaemia by administering an effective amount of a taurolin composition.

U.S. Pat. No. 4,445,889 discloses a method for preventing an infection in a patient introduced through a indwelling catheter, the method comprising, connecting the patient to the catheter, connecting the catheter to a fluid receiving container, admitting into the container a biocidal dispensing device, and releasing a biocide into fluid in the container for inhibiting the growth of infectious bacteria in the container and concomitantly their introduction into the catheter and the patient.

U.S. Pat. No. 4,587,268 discloses a composition for the treatment of wounds comprising a resorbable aqueous gel having dissolved or dispersed therein one or more water-soluble medicaments, which are preferably an antibiotic or a methylol transfer antibacterial.

U.S. Pat. No. 4,626,536 discloses the use of taurolin compounds to combat toxic proteins or peptides, e.g., venoms, fungal toxins and bacterial exotoxins, in the bloodstream of humans or warm-blooded animals.

U.S. Pat. No. 4,797,282 discloses a drug depot, which can be implanted in the body, for the controlled, delayed release of cytostatics, comprising a synthetic material based on polyacrylates and/or polymethacrylates containing a cytostatic and at least one amino acid.

U.S. Pat. No. 4,853,225 discloses an implantable medicament depot useful for combating infections comprising physiologically acceptable excipients and at least one delayed release active compound that is a chemotherapeutic of the gyrase inhibitor type.

U.S. Pat. No. 4,960,415 discloses a device for inserting in wounds and wound cavities consisting of a container containing a pharmaceutically active substance, the walls of this container consisting at least partly of a membrane, preferably a semi-permeable membrane, which allows the active substance to escape into the wound area. The container is, more preferably, a dialysis tube. In order to drain off wound secretions, the container containing the pharmaceutically active substance, particularly taurolidine, is conveniently connected to a drainage tube. Preferably, a drainage tube is used in which the end that leads into the wound is split into filaments.

U.S. Pat. No. 5,077,281 discloses the use of taurolin compounds as blood coagulation-inhibiting agents and as abacterial inflammation-inhibiting agents. According to the patent, taurolin has outstanding coagulation-inhibiting action and is especially suitable for use in medical conditions requiring dialysis and for vascular prostheses. It is also disclosed that these compounds can be used together with other anti-coagulants such as coumarin or heparin.

U.S. Pat. No. 5,093,117 discloses pharmaceutical compositions that are said to be useful for the treatment or prophylaxis of Gram-negative bacteremia or septic shock. These compositions contain a bactericidal effective amount of polyclonal immunoglobulins against Gram-negative bacteria and a blood clot-dissolving effective amount of protein C. The compositions may further contain one or more protein C cofactors and monoclonal antibodies against Gram-negative bacterial endotoxins. A method for the treatment or prophylaxis of Gram-negative bacteremia or septic shock comprises administering, either together or separately, a bactericidal effective amount of polyclonal immunoglobulins agains Gram-negative bacteria and a blood clot-dissolving effective amount of protein C. The method may optionally include administering one or more protein C cofactors and monoclonal antibodies against Gram-negative endotoxins.

U.S. Pat. No. 5,210,083 discloses an aqueous solution containing a bacterially effective concentration of taurolidine and/or taurultam together with a parenterally acceptable polyol. The aqueous solution is said to be particularly suitable for parenteral administration.

U.S. Pat. No. 5,362,754 discloses pharmaceutical compositions of a mixture of minocycline and EDTA (M-EDTA) and methods of using the compositions in maintaining the patency of a catheter port. Methods for inhibiting the formation of polysaccharide-rich glycocalyx (such as the glycocalyx of staphylococcal organisms) are also provided using an M-EDTA solution. The M-EDTA solution may also be used to pretreat a medical device to prevent adherence of infectious organisms, such as *S. epidermis* and *S. aureus*. The compositions destroy and prevent the formation of polysaccharide-rich glycocalyx.

U.S. Pat. No. 5,545,213 discloses articles having a graft polymer with a net ionic charge bonded to a polymeric substrate surface to provide an improved method for administering a bioactive agent having a net ionic charge. The articles are said to be especially useful as thromboresistant and\or antimicrobial medical devices.

U.S. Pat. No. 5,593,665 discloses products containing tumor necrosis factor and taurolidine and/or taurultam as a combined preparation for simultaneous, separate or sequential use for treatment of patients suffering from medical conditions mediated by tumor necrosis factor.

U.S. Pat. No. 5,688,516 discloses compositions and methods of employing compositions in flushing and coating medical devices. The compositions include selected combinations of a chelating agent, anticoagulant, or antithrombotic agent, with a non-glycopeptide antimicrobial agent, such as the tetracycline antibiotics. Methods for using these compositions for coating a medical device and for inhibiting catheter infection are also disclosed. Particular combinations include minocycline or other non-glycopeptide antimicrobial agent together with EDTA, EGTA, DTPA, TTH, heparin and/or hirudin in a pharmaceutically acceptable diluent.

U.S. Pat. No. 5,718,899 discloses compositions containing a high concentration of the full repertoire of immunoglobulins that are used to combat infections from microorganisms and viruses at a wound, surgical, or burn site, or normal tissue at times of risk of infection. The compositions are applied directly to a wound or burn site as an ointment, creme, fluid, spray, or the like, prior to vital or bacterial attachment or biofilm formation such that adhesion of the pathogens is inhibited and the pathogens closest to the wound or burn site will be pre-opsonized for phagocytic killing prior to toxin release. The immunoglobulins in the composition can be immobilized on a biocompatible material such as collagen, fibrin, hyaluronan, biodegradable polymers, and fragments thereof, which will be placed in situ at the wound, surgical, or burn site. In addition, the immunoglobulins in the composition may be coated on the body contacting surface of an implantable device such as a catheter, contact lens or total joint. The compositions are said to have particular application in preventing infections.

U.S. Pat. No. 5,752,941 discloses central venous polyurethane catheters having a thin hydrophilic coating loaded with an antibiotic of the ramoplanin or any mixture thereof and their use in preventing catheter related infections. These catheters are said to be useful to prevent bacterial adherence and colonization and, therefore, to lower risk of vascular infections in catheterized patients. The method of preparing the catheter of the invention consists in incubating polyurethane catheters coated with a hydrophilic film in an aqueous solution of the selected antibiotic.

U.S. Pat. No. 5,783,570 discloses an organic solvent-soluble mucopolysaccharide consisting of an ionic complex of at least one mucopolysaccharide (preferably heparin or heparin derivative) and a quaternary phosphonium, an antibacterial antithrombogenic composition comprising said organic solvent-soluble mucopolysaccharide and an antibacterial agent (preferably an inorganic antibacterial agent such as silver zeolite), and to a medical material comprising said organic solvent soluble mucopolysaccharide. The organic solvent-soluble mucopolysaccharide, and the antibacterial antithrombogenic composition and medical material containing same are said to easily impart antithrombogenicity and antibacterial property to a polymer to be a base material, which properties are maintained not only immediately after preparation of the material but also after long-term elution.

U.S. Pat. No. 5,788,979 discloses a method for coating a biomaterial to be placed in contact with a patient's blood flow to inhibit blood coagulation from adhering to the biomaterial that would otherwise result from such contact. A biodegradable material of liquid state compatible with the blood and tissue of the human body is prepared, and an anti-coagulant drug is incorporated into the liquid state of the biodegradable material to form a liquid coating material. The liquid coating material is adhesively applied to a surface of the biomaterial in a substantially continuous overlying layer having a formulation, pattern and thickness selected according to the period of time over which the coating material is to perform its anti-coagulant action. Thereafter the coating material is dried to a layer thickness less than about 100 microns for continuous disintegration thereof as a function of time when the layer is in contact with flowing blood.

Gorman et al., *J. Clin. Pharm. Ther.* 12:393–399 (1987) reported the examination of three antimicrobial agents, taurolidine, chlorhexidine, and povidone-iodine for microbial anti-adherence activity. Two adherence systems were investigated: an oral isolate of *Candida albicans* to human buccal epithelial cells and a urine isolate of *E. coli* to human uroepithelial cells. Each of the three agents exhibited significant anti-adherence activity, which was concentration dependent.

Root et al., *Antimicrobial Agents and Chemotherapy* 32(11):1627–1631 (1988) reported that granulocytopenic patients with an intravascular catheter are at increased risk for infection with *S. epidermis*. During the intervals when the catheters are not being used for infusions, it is customary to maintain patency of the catheter lumen with a solution containing heparin. The authors showed that heparin does not inhibit the growth of *S. epidermis* isolated from the catheter of an infected patient. A 20-mg/mL solution of disodium EDTA, a chelating agent that effectively anticoagulates blood at this concentration, was shown to be bactericidal for an initial inoculum of $10^3$ CFU of staphylococci per mL in 24 hours. Vancomycin, an antibiotic that is often employed to treat Staphylococcus infections was also found to be bactericidal for initial inocula of $10^3$ CFU/mL at doses of 6.7 µg/mL, a drug concentration in the therapeutic range. The authors recommended that EDTA be studied as a replacement for heparin solutions for the maintenance of intravenous catheters in granulocytopenic patients, in view of its low cost, effectiveness as an anticoagulant, and bactericidal activity.

Jones et al., J. Appl. Bacteriol. 71:218–227 (1991) examined the effects of three non-antibiotic, antimicrobial agents—taurolidine, chlorhexidine acetate, and povidone-iodine—on the surface hydrophobicity of the clinical strains *E. coli, S. saprophyticus, S. epidermidis*, and *C. albicans*. At concentrations reported to interfere with microbial-epithelial cell adherence, all three agents were found to alter the cell surface hydrophobicity. However, these effects failed to exhibit a uniform relationship. Generally, taurolidine and povidone-iodine treatments decreased the hydrophobicity of the strains examined, whereas chlorhexidine acetate effects depended upon the micro-organism treated.

Traub et al., *Chemotherapy* 39:322–330 (1993) examined taurolidine for bactericidal activity against a representative number of multiple-antibiotic-resistant bacterial isolates in broth as well as in the presence of bovine and human serum and fresh defibrinated human blood. The authors suggested that this antimicrobial substance might be employed for topical treatment of patients colonized or superficially infected by glycopeptide-resistant strains of *E. faecium, S. aureus* (GRMRSA), or by Enterobacteriaceae producing wide-spectrum β-lactamases.

Willatts et al., *Crit. Care Med.* 23(6): 1033–1039 (1995) reported that taurolidine had no beneficial therapeutic effect on the outcome of patients admitted to the intensive therapy unit of a university teaching hospital with sepsis syndrome, using clinical, bacteriologic outcomes, progression of endotoxemia, resolution of organ failure, and 28-day mortality rate as end points.

Darouiche et al., *Nutrition* 13(4)(suppl):26S–29S (1997) reported that the prevention of vascular catheter-related infection mostly centers around inhibiting the adherence to the catheter of microorganisms originating from either the skin or the catheter hub. They described two general approaches that can be used non-exclusively for the successful prevention of vascular catheter-related infection. The first approach does not use antimicrobial agents and includes measures such as placement and maintenance of vascular catheters by a skilled infusion therapy team and use of maximal sterile barriers. The second approach uses antimicrobial agents and involves the application of topical disinfectants such as chlorhexidine, use of silver-impregnated subcutaneous cuffs (for short-term central venous catheters), flushing catheters with a combination of antimicrobial and antithrombic agents, and coating of catheters with either antiseptic (chlorhexidine and silver sulfadiazine) or antimicrobial agents (minocycline and rifampin).

In a talk presented at the 30th annual meeting of the American Society of Nephrology, held Nov. 2–5, 1997 in San Antonio, Tex., Sodemann et al. reported on a four year trial of a gentamicin/sodium citrate mixture as an antibiotic-lock technique for salvage and prevention of catheter-related infections. They concluded that the replacement of catheters due to infection can be avoided by routine application of the concentrated gentamicin/citrate mixture and that even the salvage of intraluminally contaminated catheters is possible.

The disclosures of the foregoing are incorporated herein by reference in their entirety.

Notwithstanding the above-described contributions to the art, a need continues to exist for a safe and effective method for the prevention of infection and blood coagulation in patients whose illness requires the implantation of internal prosthetic devices, e.g., catheters and ports.

SUMMARY OF THE INVENTION

In accordance with the present invention, biocidal/anticoagulant compositions are provided for use in flushing and coating internal prosthetic devices, especially catheters and ports.

The present invention is directed to an internal prosthetic device comprising:
(a) means for providing a continuous flowpath, crossing a patient's skin, between an external-to-patient site and an internal-to-patient site;
(b) means for blocking the flowpath; and
(c) a biocidal lock comprising:
  (i) an anticoagulant; and
  (ii) a non-antibiotic biocide.

More particularly, the present invention is directed to an internal prosthetic device access system comprising:
(a) means for providing a continuous flowpath, crossing a patient's skin, between an external-to-patient site and an internal-to-patient site;
(b) means for blocking the flowpath at a point under the patient's skin;
(c) means for removing the flowpath portion crossing the patient's skin; and
(d) a biocidal lock comprising:
  (i) an anticoagulant; and
  (ii) a non-antibiotic biocide.

In a particularly preferred embodiment, the present invention is directed to a hemodialysis access system comprising:
(a) means for providing a continuous flowpath, crossing a patient's skin, between and external-to-patient dialysis site and an internal blood vessel of the patient, the means including a flow conduit having no more than gentle changes in direction and whose internal surfaces are smooth and free of abrupt changes in flow area and define a flowpath sized for hemodialysis flow rates, and free of obstructions to provide low flow resistance and avoid any stagnation point;
(b) means for blocking the flowpath at a point under the patient's skin;
(c) means for removing the flowpath portion crossing the patient's skin; and
(d) a biocidal lock comprising:
  (i) an anticoagulant; and
  (ii) a non-antibiotic biocide.

In another preferred embodiment, the present invention is directed to a hemodialysis access system for access for a human or animal patient's vascular system for high fluid flow rate exchange of blood between the vascular system and an external processing apparatus at a volumetric flow rate in excess of 100 mL/minute and having a decreased proclivity for effecting infection and blood coagulation, and comprising, in combination, (a) a needle assembly comprising a lumen defined by an interior surface and constructed and arranged for puncturing the skin of the patient and for carrying blood therethrough at a flow rate consistent with the high blood flow requirement of the blood exchange process;

(b) a subcutaneously implantable access device permitting fluid connection to a vessel or space within a patient's body, the device comprising:
   (i) a channel structure providing a flowpath having a straight or gently changing flow direction and having an interior surface and a distal end and a proximal end with reference to the patient's skin puncture site and constructed and arranged for insertion of the needle through the proximal end of the channel and withdrawal of the needle therefrom,
   (ii) a seal arranged within the channel and movable between first and second positions, where the seal, in the first position, with the needle not inserted through the seal, prevents fluids from passing the seal and, in the second position, with the needle inserted through the seal, allows fluids to pass through the needle and emerge substantially at the channel distal end, and where blood flowpath transitions between the needle interior surface and the channel interior surface are substantially continuous and smooth when the means for sealing is in the second position; and the device further comprising structure for joining the channel distal end to a catheter that extends to an internal vessel of the patient's body, and wherein such joining is continuous and smooth along the interior surfaces of the channel and catheter; and (c) a biocidal lock comprising:
   (i) an anticoagulant; and
   (ii) a non-antibiotic biocide.

In a particularly preferred embodiment, the access system further comprises a catheter constructed and arranged for implantation between the device at a proximal catheter end and to or into a patient's blood vessel at a distal catheter end and means for attaching the catheter to the surrounding patient tissue.

BRIEF DESCRIPTION OF THE DRAWINGS

FIG. 1 is a cross-sectional view of an implanted access device of the present invention;

FIG. 2 is a cross-section of a second embodiment of the device of the present invention;

DESCRIPTION OF THE PREFERRED EMBODIMENTS

Figure 3:
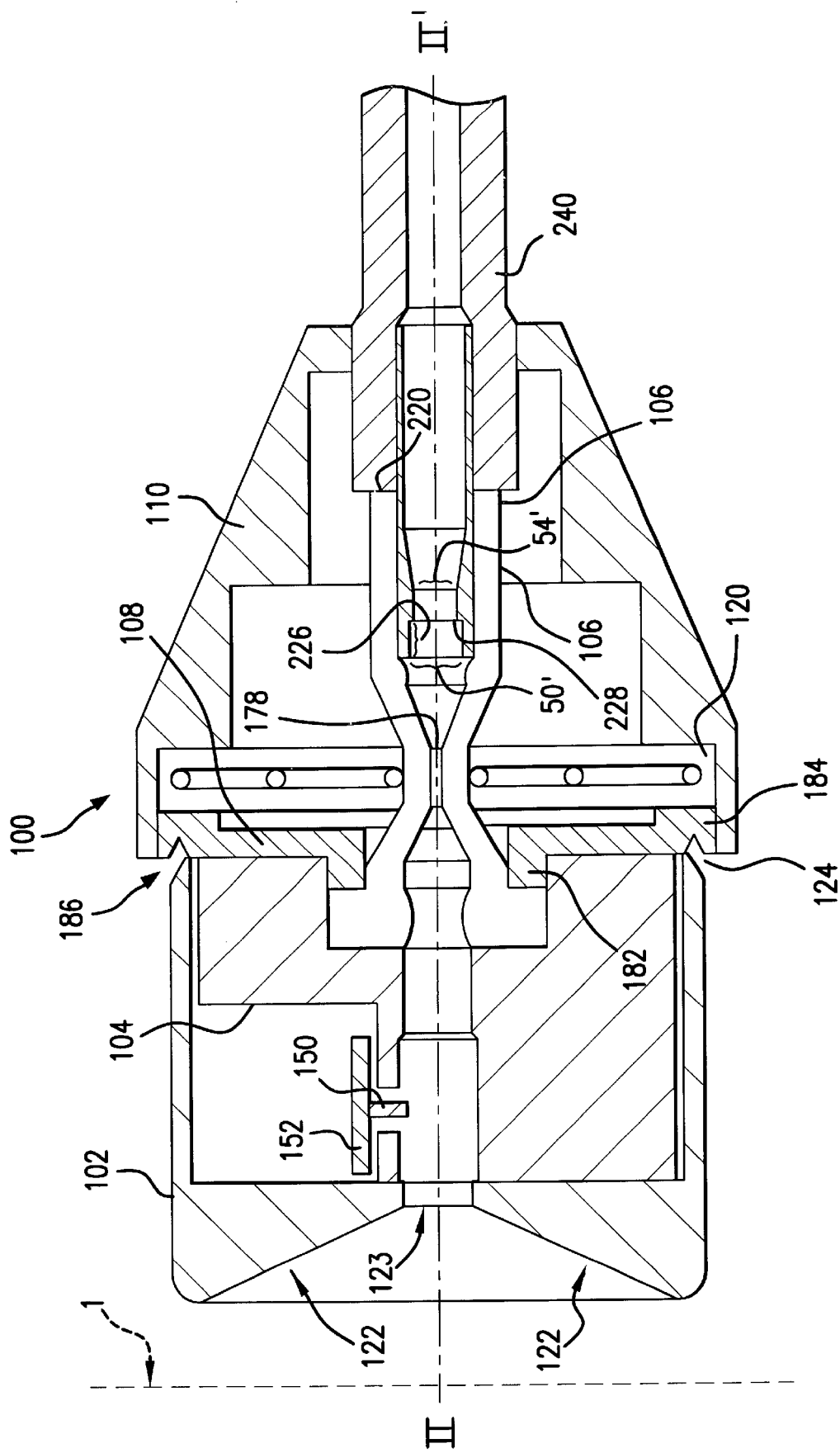
FIG. 3 is a cross-section of a third embodiment of the device of the present invention.

As stated above, in a preferred aspect, the present invention is directed to an internal prosthetic device access system comprising:

(a) means for providing a continuous flowpath, crossing a patient's skin, between an external-to-patient site and an internal-to-patient site;

(b) means for blocking the flowpath at a point under the patient's skin;

(c) means for removing the flowpath portion crossing the patient's skin; and (d) a biocidal lock comprising:
   (i) an anticoagulant; and
   (ii) a non-antibiotic biocide.

Preferably, the present invention is directed to a hemodialysis access system for access for a human or animal patient's vascular system for high fluid flow rate exchange of blood between the vascular system and an external processing apparatus at a volumetric flow rate in excess of 100 mL/minute and having a decreased proclivity for effecting infection and blood coagulation, and comprising, in combination, (a) a needle assembly comprising a lumen defined by an interior surface and constructed and arranged for puncturing the skin of the patient and for carrying blood therethrough at a flow rate consistent with the high blood flow requirement of the blood exchange process;

(b) a subcutaneously implantable access device permitting fluid connection to a vessel or space within a patient's body, the device comprising
   (i) a channel structure providing a flowpath having a straight or gently changing flow direction and having an interior surface and a distal end and a proximal end with reference to the patient's skin puncture site and constructed and arranged for insertion of the needle through the proximal end of the channel and withdrawal of the needle therefrom,
   (ii) a seal arranged within the channel and movable between first and second positions, where the seal, in the first position, with the needle not inserted through the seal, prevents fluids from passing the seal and, in the second position, with the needle inserted through the seal, allows fluids to pass through the needle and emerge substantially at the channel distal end, and where blood flow path transitions between the needle interior surface and the channel interior surface are substantially continuous and smooth when the means for sealing is in the second position; and the device further comprising structure for joining the channel distal end to a catheter that extends to an internal vessel of the patient's body, and wherein such joining is continuous and smooth along the interior surfaces of the channel and catheter; and (c) a biocidal lock comprising:
        (i) an anticoagulant; and
        (ii) a non-antibiotic biocide.

As employed herein, a "biocidal lock solution" is a solution of a biocidal lock that displaces body fluid, e.g., blood, from an internal prosthetic device, e.g., the lumen of a catheter, making the lumen space inhospitable to microorganisms and preventing the clotting of residual blood in the device.

The preferred subcutaneously implantable device of the present invention includes (a) an access guidance means having a through channel and (b) a catheter having a through channel and comprising an access portion, a sealing portion, and a distal portion. A resilient means for sealing is arranged within the sealing portion of the catheter. The resilient means for sealing ordinarily prohibits fluids from passing the seal. But when a mechanical device is inserted percutaneously, and guided to the catheter's access portion by the access guidance means, the mechanical device passes through the access portion of the catheter, engages the sealing means, and pushes it open. This provides access to the catheter's distal portion and, ultimately, the vessel lumen, as the distal portion of the catheter, distal from the access guidance means, extends into a vessel lumen. The catheter is attached to the surrounding tissue supporting the catheter.

The means for sealing includes, in a preferred embodiment, a tube made of a resilient material, which incorporates a valving feature within the tube lumen. The tube is disposed axially along the inner wall of the channel. A spring clamp is provided adjacent to and external of the tube and acts to compress the tube such that the tube's inner lumen is closed, thereby preventing fluids from passing.

The spring clamp is arranged and constructed to close the tube's lumen, such that the longitudinal transition profile from the open to the closed position forms a particular shape. The shape of the valve allows for the conical point of the needle obturator to open or push apart the rubber valve slit in a wedging action as the needle is pushed through the seal. The needle pushing force overcomes the spring biasing force and the seal's internal stresses as the needle enters the sealing area without cutting the rubber. Because no cutting occurs, no rubber particles are generated, as seen with septa in ports. Furthermore, the number of penetration cycles to failure is very high, as negligible damage occurs during penetration.

The flow path transitions between the needle, the tube lumen, and a catheter are arranged and constructed to provide for maximum smoothness and continuous flow paths without abrupt changes in flow diameter and with no more than gentle changes in flow direction, preferably with no changes is flow direction at all. All narrowing and broadening of the flow path is gradual, with angles of 25 degrees or less. Any changes in flow direction are gentle, i.e., having bend angles that are preferably less than or equal to about 20 degrees and in any event less than or equal to 30 degrees and, simultaneously, bending radii, if any, greater than or equal to about two times the diameter of the flow path.

The device of the present invention also provides for a hollow needle apparatus that matingly corresponds to the through channel of the access device, and an obturator that is inserted into the lumen of the needle, filling the lumen. This needle/obturator combination provides a needle assembly with a pointed end, and an outer surface having smooth transitions, which are formed to puncture tissue easily and to open the valve without damaging it.

The access device of the present invention is suitable for both single-needle and standard hemodialysis, plasmapheresis, and fluid exchange therapy applications, such as, peritoneal dialysis. For standard applications, which require two flow paths, the housing can be arranged and constructed to engage two needle assemblies, as described above, and include dual-lumen through channels. When two needles are used, a bar can be provided that engages each needle, thereby locking both needles to each other to preclude inadvertent disconnection of only one needle, thereby enhancing patient safety.

It is important to note that the implantable, subcutaneous access device of the present invention is suitable for applications requiring flow rates of 100 mL/min or greater, preferably 200 mL/min or greater, with low pressure drops along a streamlined flow path having substantially no stagnation points. Low pressure drops and substantial elimination of stagnation points are achieved by having smooth transition points where different elements of the device abut (e.g., the channel-catheter interface) and by having all changes in lumen diameter be of no more than a gradual nature and having a straight or nearly straight flow path (i.e., with, at most, only gentle changes in flow direction) without sharp curves or objects protruding into the flow path and no dead volume.

Because such large flow rates are desired with low resistance, it is necessary to employ the largest needle outside diameter that patients will accept. Accordingly, rigidity of the puncture needle is desirable. A rigid needle allows a greater inner lumen diameter per outer component diameter (i.e., thinner walls) than does a flexible tube. This is important because it permits the needle to be as small as possible, thereby lessening the trauma on the patient's puncture site, while still being capable of handling large flow rates. Flexible tubes have much higher outer diameter to inner diameter aspect ratios. Thus, to accommodate the blood flows common during hemodialysis, a much larger outer diameter would be required if flexible materials, rather than rigid materials, were used. Also, a rigid needle allows a greater force to be transmitted to the seal to overcome the resistant force generated by the spring. Thus, a greater resistant force can be employed, resulting in a more robust, reliable, and fault-tolerant seal.

Further, the lack of sharp angles or bends in the flow path is much less injurious to fragile hematocytes. Since the flow path from needle to catheter (or vice versa) is straight or substantially straight, with no more than gentle changes in flow direction, if any, turbulence is minimized, and shear stresses are lessened, resulting in reduced erythrocyte damage and tendency toward platelet activation.

In its simplest form, as shown in FIG. 1, the device of the present invention comprises a modified catheter 2—which may be situated subcutaneously, as indicated by skin line 1—having an access segment 4, a distal segment 6, and an integral valve segment 8 disposed therebetween. Modified catheter 2 has throughout most of its length a standard inner diameter and a standard outer diameter 12. However, there are several distinct deviations from these values in order to achieve the functional purposes of the invention.

Access segment 4 has disposed at its terminal end a raised identification ring 14 that enables an operator to locate the subcutaneous access device entrance 16. Access segment 4 has an inwardly directed conical access guidance portion 18 and an access alignment portion 20. Access guidance portion 18 has an initial inner diameter 22 greater than standard valve inner diameter 10 that gradually tapers inwardly until standard valve inner diameter 10 is achieved. Thus, upon insertion, conical access guidance portion 18 guides the percutaneous mating needle 40 into the access alignment portion 20, where the needle 40 having needle end 48 is aligned with valve slit 28. Needle 40 has an outer barrel diameter 50, compatible with standard valve inner diameter 10, and an inner barrel diameter 54. Needle 40 is provided with an obturator 42 having a conical tip for percutaneous insertion of needle 40 into the device without tissue becoming lodged in the lumen of needle 40.

Integral valve segment 8 comprises a tapered valve access portion 24 and a valve portal 26 to further align needle 40 with valve slit 28. It is important to note that integral valve segment 8 is most preferably molded with a solid valve seal portion 30 that has valve slit 28 later formed therethrough. This construction results in a more complete seal and requires less sealing force than does a flattened tube.

Integral valve segment 8 further comprises an opposing tapered distal portion 32 and has formed into its exterior, in radial alignment with valve seal portion 30, a valve sealing means seat 34, which is a circumferential depression in the segment exterior such that the catheter outer diameter through valve sealing means seat 34 is less than the standard outer diameter 12, but greater than standard inner diameter 10. Valve sealing means seat 34 accommodates valve sealing means 36, which provides a radial biasing force sufficient to close valve seal portion 30, and keep it closed while the device is not in use. In an alternate embodiment, valve sealing means 36 may have one or more mounting tabs 38 formed therefrom or attached thereto. During implantation, the one or more mounting tabs 38 are attached to surrounding tissue such that catheter 2 is immobilized throughout integral valve segment 8, but allows lateral movement of access segment 4 under the skin.

Outflow segment 6 is implanted such that its terminal end is disposed within the vessel or space to which access is desired. To begin treatment, an operator first locates access segment 4 through the skin using raised identification ring 14 as a guide. The operator punctures the skin with obturator 42 disposed within needle 40 such that the needle-obturator assembly enters access guidance portion 18 and is aligned by access alignment portion 20. Continuing to be inserted into the device, the needle-obturator assembly encounters valve access portion 24 and valve portal 26. As the tip of obturator 42 enters valve portal 26, the tapered leading edge of obturator 42 presses against valve access portion 24, overcoming the radical biasing force exerted by valve sealing means 36 and thereby opening valve slit 28 such that needle 40 may pass through the valve seal portion 30. This is accomplished without damage to valve seal portion 30 because needle 40 has already been axially aligned with valve slit 28 by the access alignment portion 20. This process is much smoother and causes less discomfort to the patient when the needle is provided with a medically acceptable, water-based lubricant prior to insertion.

It is important to note that because integral valve segment 8 is formed in a closed fashion and valve slit 28 later opened, and also because of the sealing properties of the material from which catheter 2 is made, the valve of the present invention achieves a complete seal with minimal biasing forces required to be exerted by valve sealing means 36. Accordingly, the force that must be imparted by the needle/obturator combination in order to overcome this biasing force to allow entry of the needle/obturator combination into the valve is substantially less than would be required to close known valves, which are essentially flattened tubes and which never achieve a complete seal, unless substantially greater biasing forces are used. This diminution of force results in less jarring of the device during needle insertion and withdrawal, thereby greatly enhancing patient comfort.

In a second embodiment, as shown in FIG. 2, it is contemplated that distal segment 6 is attached to a standard medical catheter 44 by insertion therebetween of adapter 56. Adapter 56 has a first end, disposed within distal segment 6, and a second end, disposed within catheter 44, tapered such that the streamlined flow path is minimally disturbed. In addition, adapter 56 has formed within its first end a needle seating region 58 having an inner diameter 50' that corresponds with outer barrel diameter 50 of needle 40. Needle seat 58a extends radially inwardly such that its inner diameter 54' corresponds with inner barrel diameter 54 of needle 40. In this embodiment, when the needle-obturator assembly is inserted into the device and axially through the seal, needle 40 will seat against needle seat 58a such that the streamlined flow path is minimally disturbed, if at all. (See FIG. 1, not shown in FIG. 2).

In a third embodiment, as shown in FIGS. 3–8, an implanted access device 100 rests below the skin line 1. The access device 100 comprises an assembly of guidance housing 102, locking mount 104, valve 106, valve seating mount 108, valve sealing means 120, adapter 220, catheter 240, and distal housing 110, all arranged about axis AA'. The flow path through the device, shown as Axis AA', is capable of accommodating gentle changes in flow direction. In no case does a gentle change in flow direction, if present, include a bend angle exceeding about 30 degrees, and preferably not exceeding 20 degrees, within a bending radius of less than about two times standard inner diameter 10. More preferably, any such gentle change in flow direction is no more than about 20 degrees within a bending radius of at least about four times standard inner diameter 10. Standard inner diameter 10 is typically between about 0.060 and about 0.105 inch.

Guidance housing 102 is a modified hollow cylinder having a partially closed first end formed into an inwardly directed conical needle guidance surface 122 that defines an axial access lumen 123 sized to accommodate a needle suitable for use in hemodialysis, plasmapheresis, and fluid exchange therapies. Guidance housing 102 has an open second end provided with a chamfered leading edge 124.

Locking mount 104 defines lumen 143 capable of accommodating a needle suitable for use in hemodialysis, plasmapheresis, and fluid exchange therapies formed therethrough. Locking mount 104 comprises a locking, or activating, portion 140, having lock surface 144 with lock lumen 145 formed therein such that lock lumen 145 communicates with lumen 143, and a valve mounting portion 142, having formed therein valve seat 146 with cross-sectional diameter 146'. Locking portion 140 has attached thereto lock biasing means 152 such that lock biasing means 152 movably covers lock lumen 145. Locking means 150 is disposed within lock lumen 145 and is biased toward lumen 143 by lock biasing means 152. When needle 40 is inserted into lumen 143, the conical tip of obturator 42 overcomes the biasing force exerted on locking means 150 by lock biasing means 152, thereby causing locking means 150 to retract as needle 40 is inserted. When needle 40 is fully inserted into needle seat 148, semicircular locking groove 44 is aligned with locking means 150. Rotation of needle 40 allows lock biasing means 152 to push locking means 150 into semicircular locking groove 44A, thereby locking the needle 40 into the access device 100. To withdraw needle 40 from access device 100, needle 40 is again rotated so that locking means 150 again retracts and needle 40 is freely removed.

Valve 106 has an access segment 160, a distal segment 164, and an integral valve segment 162 disposed therebetween. Access segment 160 has disposed at its terminal end a raised seating ring 166 having an outer cross-sectional diameter 166' and defining valve entrance 163. Integral valve segment 162 comprises a tapered valve access portion 170 and, optionally, a valve portal 172 to further align needle 40 with valve slit 178. Integral valve segment 162 further comprises an opposing tapered distal portion 174. It is important to note that integral valve segment 162 is most preferably molded with a solid valve sealing portion 176, which has valve slit 178 later formed therethrough. This construction results in a more complete seal and requires less sealing force than does a flattened tube.

Valve seating mount 108 is a disk-shaped member having an outer cross-sectional diameter 108', a first side oriented toward valve access segment 160, and a second side oriented toward valve distal segment 164. Valve seating mount 108 defines seating mount lumen 183 having a cross-sectional diameter 183' capable of accommodating valve 106. The first side of seating mount 108 has a circumferential groove 186 disposed just axially of its outer peripheral edge. The first side of seating mount 108 also has a raised valve seating spacer 182 formed thereon. Valve seating spacer 182 has an outer cross-sectional diameter 182' substantially similar to valve seating ring cross-sectional diameter 166'. Thus, when valve 106 is inserted into seating mount lumen 183, valve seating spacer 182 and valve access ring 166 have substantially the same cross-sectional diameter and matingly fit recessed valve seat 146 in locking mount 104. This construction further prevents undesirable lateral movement of seating mount 108 relative to locking mount 104, thereby enhancing the stability of access device 100 and minimizing patient discomfort. The second side of seating mount 108 has disposed about its outer peripheral edge a raised valve sealing means spacer 184 of sufficient axial thickness to optimally position valve sealing means 120 relative to valve sealing portion 176.

Valve sealing means 120 may be any conventional or suitable sealing means capable of exerting a radial sealing force sufficient to seal valve slit 178, similar to valve slit 28 of FIG. 1.

Adapter 220, has a first end, disposed within distal segment 164, and a second end, disposed within catheter 240, tapered such that the streamlined flow path is minimally disturbed. In addition, adapter 220 has formed within its first end a needle seating region 226 having an inner diameter 50' that corresponds with outer barrel diameter 50 of needle 40. Needle seat 228 extends radially inwardly such that its inner diameter 54' corresponds with inner barrel diameter 54 of needle 40. In this embodiment, when the needle-obturator assembly is inserted into the device and axially through the seal, needle 40 will seat against needle seat 228 such that the streamlined flow path is minimally disturbed, if at all.

Catheter 240 may be of a type typical of those used in hemodialysis, plasmapheresis, and fluid exchange therapies.

Distal housing 110 has a first end with an inner cross-sectional diameter 110' sufficient to accommodate valve seating mount 108 having an outer cross-sectional diameter 108'. In addition, the first end of distal housing 110 has formed therein valve sealing means retainer 112 capable of optimally positioning valve sealing means 120 relative to valve sealing portion 176. Distal housing 110 further has a second end having formed therethrough a lumen 113 capable of accommodating catheter 240.

The cross-section of the needle 40 includes a locking groove 44. Upon insertion of needle 40 into device 100, locking means 150 extends into locking groove 44 to lock the needle 40 in position. The force exerted by lock biasing means 152 on locking means 150 is designed to allow a firm pull to disengage the locking groove 44 from the locking means 150. In another preferred embodiment, locking groove 44 is discontinuous around the circumference of the needle, and disengagement of locking means 150 from locking groove 44 is accomplished by rotating the needle 40 and then withdrawing the needle 40 for inactivation.

For hemodialysis, plasmapheresis, and other fluid exchange therapy operations where flow rates of 200 to 500 mL/minute are possible, the needle 40 can be from 15 to 17 gauge. In such operation the pressure drop through the needle 40 should not exceed 200 mm Hg. Under these conditions a needle 40 can be made of stainless steel and have a wall thickness of approximately 0.1 mm, thereby providing sufficient strength with high safety factors. In contrast, the use of flexible materials would require a needle wall thickness three to five times greater in order to prevent buckling and collapse during insertion.

In the assembled access device 100, valve 106 is disposed within lumen 183 of valve seating mount 108, the combination being seated against locking mount 104, as described above, which combination in turn is entirely disposed within guidance housing 102. Chamfered leading edge 124 of guidance housing 102 matingly fits circumferential groove 186 disposed just axially of the outer peripheral edge of valve seating mount 108. Guidance housing 102 is attached to valve seating mount 108 by known means in order to create a fluid-tight seal. Valve sealing means 120 is optimally positioned by valve sealing means spacer 184 and valve sealing means retainer 112 to seal valve sealing portion 176. Adapter 220 is disposed partly within valve distal segment 144 and partly within catheter 240, as described above. Adapter 220 has needle seating region 226 that matingly fits within needle 40, thereby creating a smooth flow path from the lumen of needle 40 to catheter 240. Valve 106, valve seating mount 108, valve sealing means 120, adapter 220, and catheter 240 are all disposed within distal housing 110. Catheter 240 emerges from distal housing 110 via axial lumen 113 formed therethrough.

Figure 4:
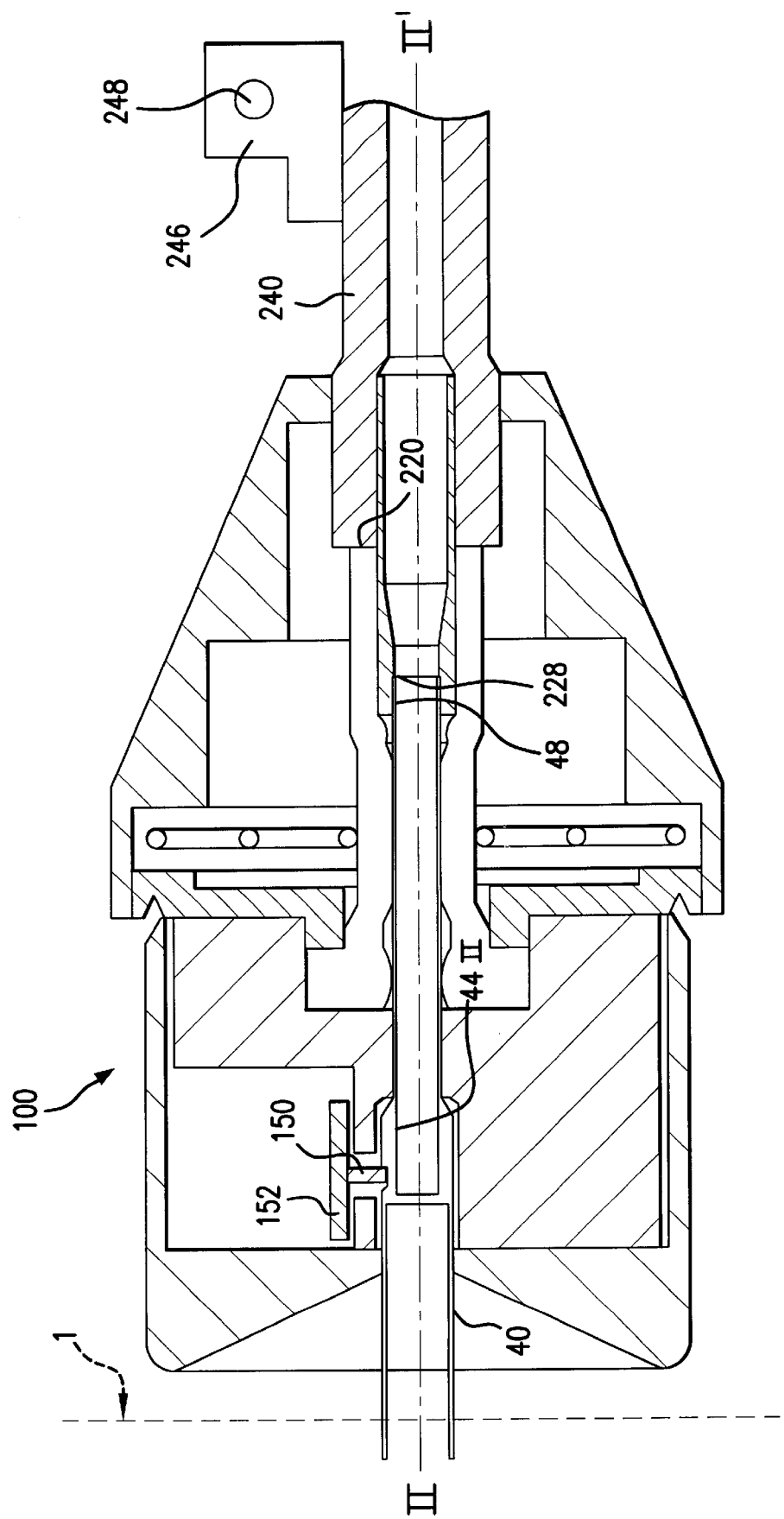
FIG. 4 is a cross-section of the embodiment shown in FIG. 3 with the needle inserted.
Figure 5:
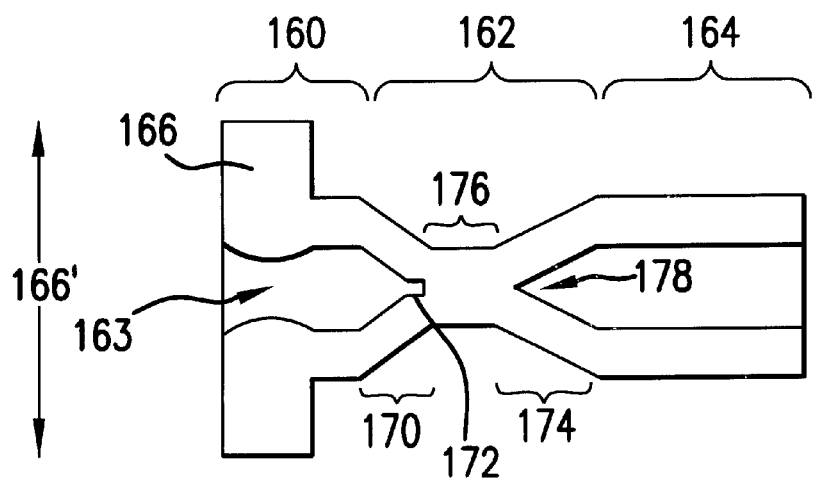
FIG. 5 is a cross-section of the valve of the embodiment shown in FIG. 3.
Figure 6:
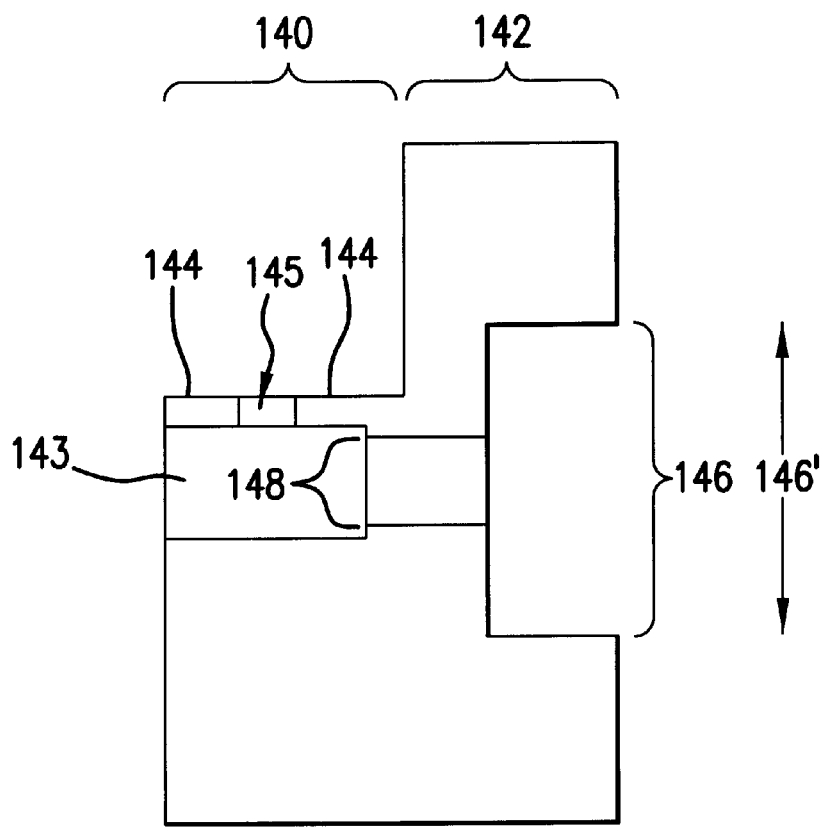
FIG. 6 is a cross-section of the locking mount of the embodiment shown in FIG. 3.
Figure 7:
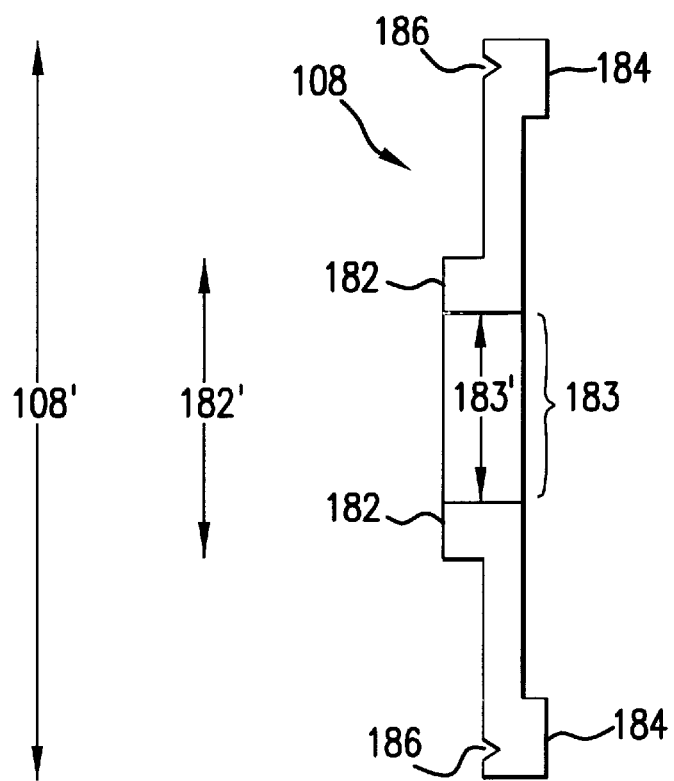
FIG. 7 is a cross-section of the valve seating mount of the embodiment shown in FIG. 3.
Figure 8:
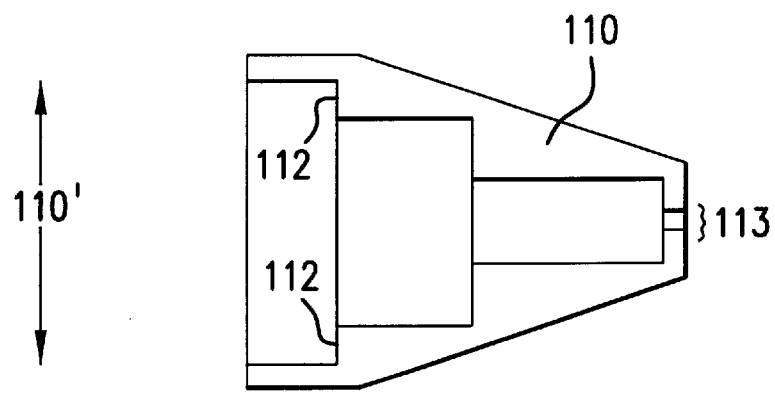
FIG. 8 is a cross-section of the distal housing of the embodiment shown in FIG. 3.

FIG. 4 shows an assembled access device 100, with needle 40 inserted and obturator 42 removed from needle 40. The needle end 48 is in contact with needle seat 228 of adapter 220, such that the transition from the inner lumen of needle 40 to the inner lumen of adapter 220 is smooth. The assembly is designed and constructed such that all the flow diameter changes are gradual and continuous. The angles of these transitions are less than 25 degrees, with less than 10 degrees preferred. Herein, flow diameter is defined as the diameter of any conduit with fluid flowing measured normal to the flow. The cross-section of the needle 40 includes a ridge and locking groove 44. The locking groove 44 is discontinuous around the circumference of the needle, and disengagement of the locking means 150 from the locking groove 44 is accomplished by rotating the needle 40 and then withdrawing the needle 40 from device 100. In another contemplated embodiment, the locking groove 44 is continuous around the circumference of the needle. The force exerted by lock biasing means 152 on locking means 150 allows the needle 40 to be withdrawn from device 100 with a firm pull to disengage the locking groove 44 from the locking means 150.

In an optional embodiment, catheter 240 has formed therefrom or attached thereto one or more tabs 246 with a through hole 248. These tabs 246 are used to fix the catheter 240, by tying or suturing, to the surrounding tissue upon implantation of device 100. The device 100 itself is not fixed to the surrounding tissue. With this arrangement, the device 100 can move underneath the skin enough to align with a needle 40 penetrating the skin without having the needle 40 move transversely to the skin. Adhesions from the tissue to the device 100 are discouraged by treating the housing surface with hyaluronic acid.

Figure 9:
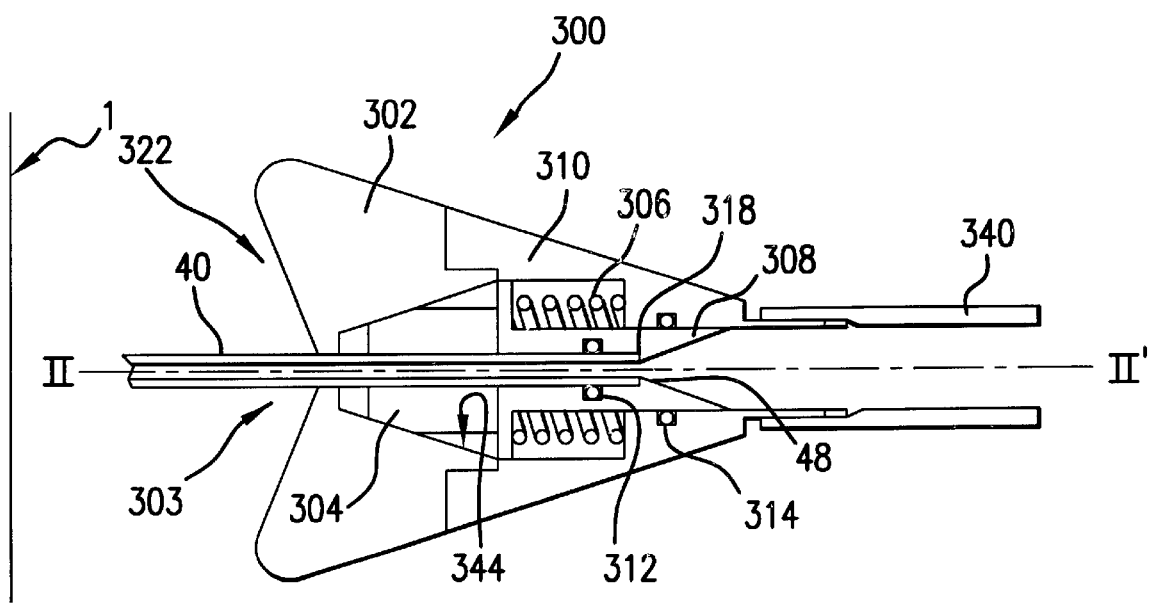
FIG. 9 is a cross-section of a fourth embodiment of the device of the present invention with a sliding seal and integral friction lock.

FIG. 9 shows another contemplated embodiment 300 where there is an integral friction lock to secure the needle 40 within the access device 300. A sealing plug 304 is disposed within housing assembly 302/310 between its access lumen 303 and the biasing force transmission flange 309 of piston 308. When the device is not in use, spring 306 biases piston 308 against sealing plug 304, urging sealing plug 304 against tapered sealing surface 344, thereby preventing fluid flow through the device.

During use, the needle 40 is guided to the access lumen 303 by the conical needle guidance surface 322 of guidance housing 302, wherein needle 40 contacts sealing plug 304. As needle 40 is pushed further into the device, the axial force exerted by needle 40 on the sealing plug 304 overcomes the sealing plug biasing force exerted on the biasing force transmission flange 309 of piston 308 by spring 306, moving sealing plug 304 away from sealing surface 344 and removing the radial compressive forces normally exerted on the sealing plug 304, sufficiently to allow needle 40 to puncture sealing plug 304. It is important to note that, unlike septa known in the art, where the needle punctures randomly, which eventually results in fragmentation of the septum, sealing plug 304 consistently is punctured in the same place and direction due to guidance of the needle 40 by the conical needle guidance surface 322 of guidance housing 302. This feature effectively eliminates sealing plug fragmentation.

Once needle 40 punctures sealing plug 304, needle 40 contacts needle seat 318 of piston 308, where the needle tip 48 contacts needle seat 318 to form a smooth transition between the needle 40 and the piston 308. Once needle 40 is inserted, sealing plug 304 provides enough residual pressure onto the needle 40 to effectively lock the needle 40 into the device 300. An axial pull on the needle 40 tends to pull the sealing plug 304 against the sealing surface 344, increasing the radial forces exerted on the needle 40, thereby holding the needle 40 even more securely. A simple twist of needle 40, however, introduces dynamic friction and allows the needle 40 to be removed from the device. O-rings 312 and 314 seal the needle 40 from the piston 308 and the piston 308 from the sealing housing 310, respectively. When the device is not in use, spring 306 biases the piston 308 towards the skin line 1, compressing the sealing plug 304 such that the sealing plug 304 seals itself, closing the passageway formed by insertion of needle 40. Note that, as the piston 308 slides relative to the catheter 340 and the sealing housing 310, the transition from the piston 308 and the catheter 340 inner wall and/or the sealing housing 310 inner wall remains smooth.

Figure 10:
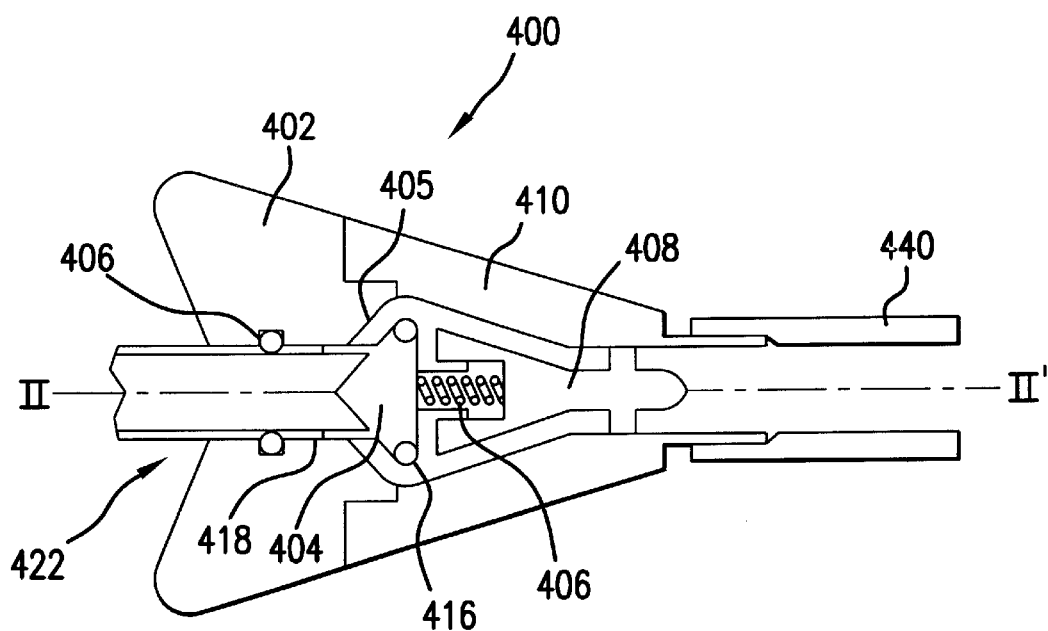
FIG. 10 is a cross-section of a fifth embodiment of the device of the present invention with a longitudinally sliding seal.

FIG. 10 is yet another contemplated valving for the present invention. In this embodiment, the needle 40 contacts a sliding spring-loaded poppet 404. As the needle 40 is pushed into the device 400 using conical needle guidance surface 422, the valve structure 408 is biased away from guidance housing 402 (as shown). The O-ring 416 leaves the housing wall 405 allowing fluid to pass through the valve. Spring 406 forces the poppet 404 and O-ring 416 back into contact with the housing wall 405 when the needle 40 is extracted from the device. The poppet 404 does not extend throughout the valve circumference, as it would then interfere with the fluid flow. Instead, the poppet 404 has a plurality of rod-like extensions 418 that provide open areas for fluid to pass through the valve when the needle 40 is inserted. The O-ring 406 provides a seal to prevent leakage around the needle 40. As piston 408 (valve structure) slides relative to the catheter 440 and the sealing housing 410 the transition from piston 408 and catheter 440 inner wall and/or sealing housing 410 inner wall remains smooth.

Figure 11:
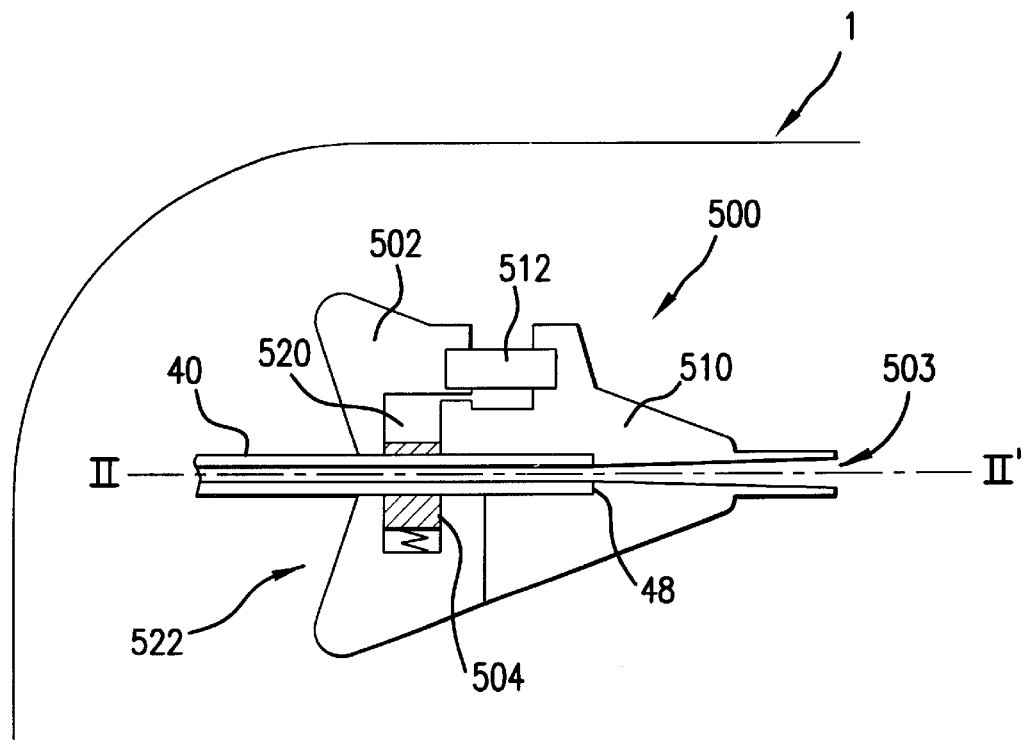
FIG. 11 is a cross-section of a sixth embodiment of the device of the present invention with a trumpet valve.
Figure 12:
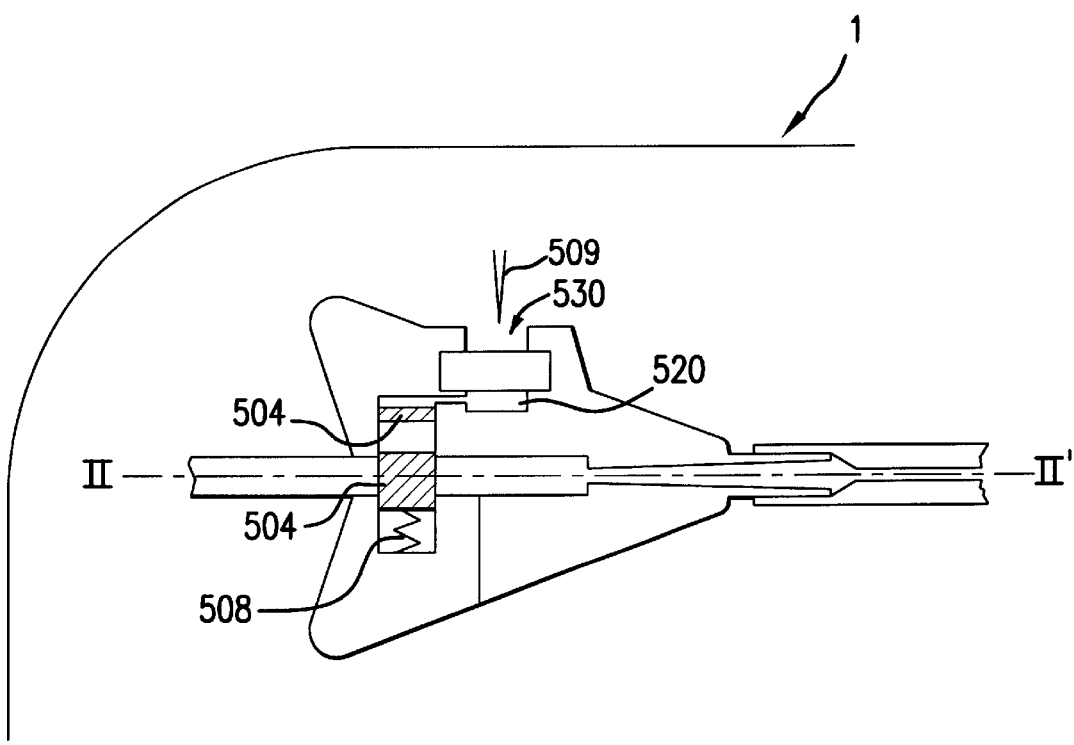
FIG. 12 is a cross-section of the embodiment shown in FIG. 11 with the needle inserted.

FIGS. 11 and 12 show another contemplated embodiment 500, wherein the valve sealing means is a trumpet valve 504. Prior to each treatment session, a fine needle 509 may be percutaneously introduced into lumen 530 and penetrate the septum 512 to open valve 504 by injecting fluid into reservoir 520 sufficient to overcome the biasing force exerted by spring 508. Needle 40 may then be introduced into the device 500, in a similar manner as described above with respect to 300 (FIG. 9) and 400 (FIG. 10), and guidance housing 502 having conical needle guidance surface 522 guides needle 40. When the treatment session is completed, needle 40 is removed from the device and a trumpet valve 504 is closed by withdrawing fluid from reservoir 520 via fine needle 509, which is then removed from the device. As shown, there is a sealing housing 510 which cooperates with guidance housing 502 and there is a seal 504 which seals passageway 503.

Figure 13:
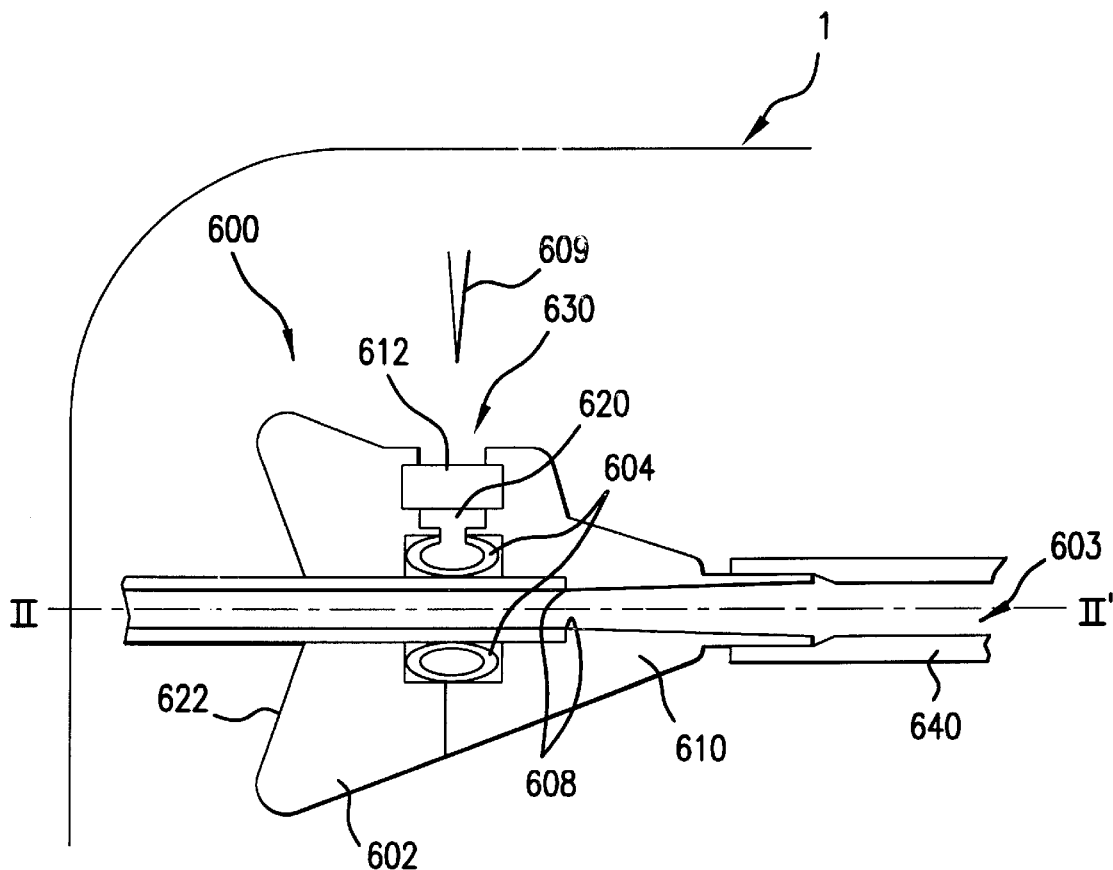
FIG. 13 is a cross-section of a fifth embodiment of the device of the present invention with an inflatable seal.

FIG. 13 is another contemplated embodiment 600 where an inflatable seal 604 seals passageway 603. The needle 40, guided by a conical needle guidance surface 522 of guidance housing 502, pushes the expandable seal 604 apart when inserted. The needle 40 then hits the stop 608 built into the sealing housing 610. When the needle 40 is extracted, the seal 604 expands, closing the passageway 603. As may be needed from time to time, a fine needle 609 may be percutaneously introduced into lumen 630 and penetrate the septum 612 to re-expand the seal 604 by injecting fluid into reservoir 620, which is in fluid connection with the lumen of seal 604. As in the other embodiments, the flow path transition from the sealing housing 610 to the catheter 640 is smooth.

Figure 14:
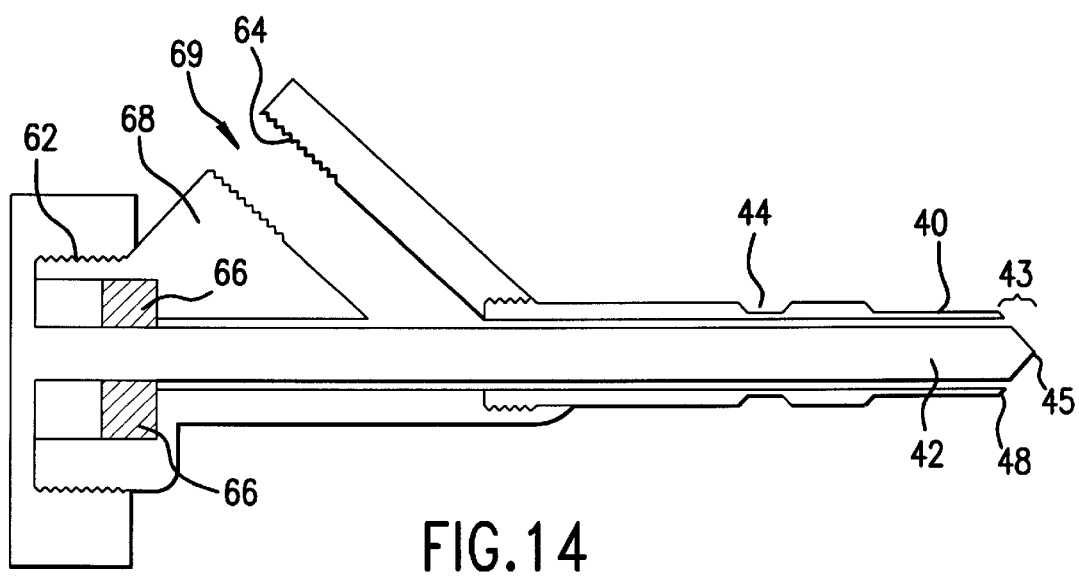
FIG. 14 is a cross-section of a preferred needle and obturator assembly.

FIG. 14 shows a preferred corresponding needle assembly constructed and arranged to mate with the previously described implanted access housings. The needle barrel 40 is of a thin metal material. Thinner material maximizes the actual flow diameter which is a general goal of any hemodialysis needle. The discomfort to the patient is reduced by smaller diameter needles, but such needles restrict flow or provide large pressure drops when high flows are forced through small needles. Low flow rates would require inordinate treatment time for hemodialysis, and high flow rates through narrow needles damage blood. There is a tradeoff and thin needle walls contribute to maximized flow diameters for a given outer needle diameter. An obturator 42 is fitted within the needle 40, providing a smooth transition 43 between the outer surface of needle 40 at the needle tip 48 and the obturator 42. The barrel of needle 40 has a semi-circular locking groove 44A. The obturator 42 is secured to a housing 68 via threads 62. The obturator 42 is necessary since the needle 40 is hollow and cannot be used to penetrate the skin because its large diameter lumen will become plugged. The obturator 42 exactly fills the hollow face presented to the skin and has a point 45 suitable for penetrating the skin. The housing 68 provides a channel 69 with the threaded fitting 64 for connecting to the hemodialysis equipment. When the obturator 42 is removed, there is a slit disk valve 66 that closes off the opening used by the obturator 42, allowing the hemodialysis to proceed.

When not in use, the internal prosthetic device of the present invention, e.g., the apparatus described above, is filled with a biocidal lock comprising an anticoagulant and a non-antibiotic biocide. As employed herein, the term "anticoagulant" is intended to mean any composition that has the ability, either directly or indirectly, to prevent the coagulation of blood or to dissolve blood clots or other coagulated species once formed. Any compound known to have this capability can be employed. As examples of such compounds may be listed di-ammonium hydrogen citrate, di-ammonium tartrate, citric acid, citric acid disodium salt, citric acid monopotassium salt, citric acid monosodium salt, citric acid tripotassium salt, citric acid trisodium salt, ethylenediaminetetraacetic acid (EDTA), EDTA diammonium salt, EDTA dipotassium salt, EDTA disodium salt, EDTA tetrasodium salt, ethylenebis(oxyethylenenitrilo)tetraacetic acid (EGTA), EDTA trisodium salt, EDTA tripotassium salt, ethylene glycol-O,O'-bis(2-aminoethyl)-N,N,N',N'-tetraacetic acid, N-(2-hydroxyethyl)ethylenediamine-N,N', N'-triacetic acid trisodium salt, nitrilotriacetic acid, potassium sodium tartrate, potassium hydrogen D-tartrate, L-tartaric acid dipotassium salt, L-tartaric acid disodium salt, L-tartaric acid monosodium salt, heparin, warfarin, acetylsalicylic acid, ibuprofen, indomethacin, prostaglandins, sulfinpyrazone, streptokinase, urokinase, tissue plasminogen activator (TPA), coumarin, protamine sulfate, anti-thrombin III, coumadin, protein C/protein S, nicoumalone, phenprocoumon, hirudin, hirulog, and the like. Mixtures of the foregoing can be employed. The preferred anticoagulant system for use in the practice of the present of this invention is a combination of citric acid and a salt thereof, preferably trisodium citrate. This is discussed in greater detail below.

The term "biocide," as used herein, means an agent that destroys, inhibits, prevents and the like, the propagation, growth, multiplication and the like of unwanted organisms. The term organisms includes microorganisms, bacteria, undulating bacteria, spirochetes, spores, spore-forming organisms, gram-negative organisms, gram-positive organisms, yeasts, fungi, molds, viruses, aerobic organisms, anaerobic organisms, mycobacteria, and the like.

The biocide employed in the practice of the present invention is one that is a "non-antibiotic," i.e., it is not an antibiotic. For purposes of the present invention, the term "antibiotic" is defined as a chemical substance produced either synthetically or by a microorganism that has the capacity, in dilute solutions, to inhibit the growth of or to kill other microorganisms. It is an object of the present invention to avoid these antibiotics in order to minimize the probability of producing microorganisms that are genetically immune thereto, although they may, if desired, be present in addition to the biocides of the invention. Preferably, the non-antibiotic biocide of the present invention is a chemotherapeutic agent.

The biocide is employed in the dialysis apparatus to kill, cleanse, prevent, and/or retard the presence or propagation of harmful or unwanted micro-organisms. The micro-organisms include the fungi Aspergillus niger, Aspergillus flavus, Rhizopus nigricans, Cladosporium herbarium, Epidermophyton floccosum, Trichophyton mentagrophytes, Histoplasma capsulatum, and the like. The term microorganisms also includes antibacterial activity against Pseudomonas aeruginosa, Escherichia coli, Proteus vulgaris, Staphylococcus aureus, Staphylococcus epidermis, Streptococcus faecalis, Klebsiella, Enterobacter aerogenes, Proteus mirabilis, other gram-negative bacteria and other gram-positive bacteria, mycobactin and the like. The term also embraces yeast such as Saccharomyces cerevisiae, Candida albicans, and the like. Additionally, spores of micro-organisms, viruses and the like, are within the intent of the invention.

The biocides used in the device can include, inter alia, a member selected from the group consisting of a phenol, quaternary ammonium, surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

Among the non-antibiotic biocides that can be employed in the practice of the present invention are, for example, acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-amino-hydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4, 4'-trichloro-2'-hydroxydiphenol, thymol, chlorhexidine, benzalkonium chloride, cetylpyridinium chloride, silver sulfadiazine, and silver nitrate.

Exemplary biocidal dyes include acridine, acriflavine, aminacrine hydrochloride, proflavin hemisulfate, triphenylmethane, magenta, crystal violet, scarlet red, pararosaniline, and rosaniline.

Exemplary chlorine releasing biocides include sodium hypochlorite, oxychlorosene, chloramine, dichlorodimethylhydantoin, halazone, dichloramine, chlorasine, succinchlorimide, trichloroisocyanuric acid, dichloroisocyanurate, trichloromelamine, dichloroglycoluril, halogenated dialkyl-hydantoin, and halane.

Exemplary biocidal quinaldinium and quinoline biocides are dequalinium, laurolinium, hydroxyquinoline, lioquinol, chlorquinaldol and halquinol.

Exemplary quaternary ammonium biocides include pyridinium biocides, benzalkonium chloride, cetrimide, benzethonium chloride, cetylpyridinium chloride, chlorphenoctium amsonate, dequalinium acetate, dequalinium chloride, domiphen bromide, laurolinium acetate, methylbenzethonium chloride, myristyl-gamma-picolinium chloride, ortaphonium chloride, and triclobisonium chloride.

Exemplary furans include griseofulvin, nitrofurfural, nitrofurazone, nitrofurantoin, furazolidone, and furaltadone.

Exemplary phenol biocides include chlorinated phenol, cresol phenol, thymol, chlorocresol, chloroxylenol, hexachlorophene, bisphenols, amylmetacresol, bithionol, chlorothymol, dichloroxylenol, chlorophene, p-chlorophenol, p-phenylphenol, trinitrophenol, dichlorobisphenol, and bromochlorobisphenol.

Exemplary lactones include propiolactone.

Exemplary urea biocides include noxytiolin, polynoxylen, and triclocarbon.

Examples of other biocides useful for the purpose of the invention are chlorhexidine gluconate, chlorhexidine, chlorhexidine acetate, chlorhexidine hydrochloride, dibromopropamidine, halogenated diphenylalkanes, dibromsalan, metabromsalan, tribromsalan, carbanilide, salicylanilide, tetrachlorosalicylanilide, trichlorocarbanilide, propamidine isethionate, pentamidine, picloxydine, mendalamine, the acid addition and quarternary, methenamine mandelate, polyoxymethylene esters such as polyoxymethylene diester, polyoxymethylene diacetate and the like, and mixtures thereof.

Antiseptics that can be employed as the biocides used in the present invention include: guanidines, such as, Alexidine, Ambazone, Chlorhexidine and Picloxydine; halogens and halogen compounds, such as, bornyl chloride, calcium iodate, cloflucarban, flurosalan, iodic acid, iodine, oxychlorosene, povidone-iodine, sodium hypochlorite, sodium iodate, symclosene, thymol iodide, triclocarban, triclosan and troclosene potassium; mercurial compounds, such as, Hydragaphen, Meralein Sodium, Merbromin, ammoniated, mercuric sodium p-phenolsulfonate, mercuric succinimide, mercuric sulfide, Red, Mercurophen, mercurous acetate, mercurous chloride, mercurous iodide, Nitromersol, Thimerfonate Sodium and Thimerosal; Nitrofurans, such as, Furazolidone, 2-(Methoxymethyl)-5-nitrofuran, Nidroxyzone, Nifuroxime, Nifurzide and Nitrofurazone; phenols such as Acetomeroctol, Bithionol, carvacrol, chloroxylenol, clorophene, cresol(s), p-cresol, fenticlorn, hexachlorophene, 1-napthyl salicylate, 2-napthyl salicylate, 2,4,6-tribromo-m-cresol, and 3',4',5-trichlorosalicylanilide; quinolines, such as, Aminoquinuride, Benzoxiquine, Broxyquinoline, Chloroxine, Chlorquinaldol, Cloxyquin, Ethylhydrocupreine, Euprocin, Halquinol, Hydrastine, 8-Hydroxyquinoline, 8-Hydroxyquinoline Sulfate and Iodochlorhydroxyquin; and others, such as, aluminum acetate solution, aluminum subacetate solution, aluminum sulfate, 3-amino-4-hydroxybutyric acid, boric acid, chlorhexidine, chloroazodin, m-cresyl acetate, cupric sulfate, Dibromopropamidine, Ichthammol, Negatol, Noxytiolin, Ornidazole, β-propiolactone, and α-terpineol.

The biocides used in the practice of the present invention also embrace the polymer paraformaldehyde. The paraformaldehyde polymer used as a biocide is selected from the group consisting of the cyclic tripolymer of the general formula $(CH_2O)_n$ where n is 3 and the linear polymer of the general formula $HO(CH_2O)_mH$ wherein m is 3 to 125. These polymers are white crystalline solids, and in the presence of moisture undergo depolymerization to yield the water soluble biocide and disinfectant formaldehyde; see the *Encyclopedia of Chemical Technology*, Kirk-Othmer, Vol. 10, page 81, 1966, published by John Wiley & Sons, Inc., New York. In operation, the paraformaldehyde is moisture-activated by fluid from the surroundings causing it to depolymerize to formaldehyde. The formaldehyde acts as a biocide, or disinfectant to control the presence of microorganisms. Generally, in the presence of moisture, or in the presence of moisture and an acid catalyst, the cyclic and linear polymers are converted up to 99% formaldehyde, which is released over a prolonged period of time.

The amount of biocide in the preparation used in the device of the present invention will generally be between about 0.001 mg/mL and about 1000 mg/mL, with a more preferred amount of between about 1 to about 200 mg/mL and a most preferred amount of between about 2 mg/mL an about 100 mg/mL. The biocides are disclosed in *Disinfection, Sterilization and Preservation*, by Block, 1977, published by Lea & Febiger, Philadelphia, Pa.; in *Inhibition and Destruction of Microbial Cells*, by Hugo, 1971, published by Academic Press, New York; and in Martindale, The Extra Pharmacopoeia, Edited by Blacow, published by The London Pharmaceutical Press, London.

In an especially preferred embodiment of the present invention, the biocide and anticoagulant are employed in a therapeutically effective amount of a composition comprising:

(A) at least one compound of the formula I

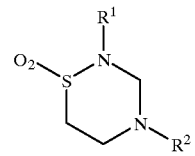

wherein $R^1$ is hydrogen or alkyl and $R^2$ is hydrogen, alkyl, or a group of the formula II

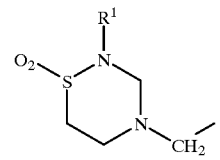

and (B) at least one compound selected from the group consisting of biologically acceptable acids and biologically acceptable salts thereof.

The preparation of representative examples of the compounds of formula I is described in U.K. Patent No. 1,124,285. Basically, these compounds are condensation products of taurinamide and formaldehyde and, therefore, will be referred to herein as "taurinamide derivatives." They are active not only against both gram-positive and gram-negative bacteria, but also against exotoxins and endotoxins produced by these organisms.

Where $R^1$ and/or $R^2$ are alkyl, they may be either straight or branched chain alkyl and are preferably independently selected from those alkyls having from 1 to 8 carbon atoms, i.e., methyl, ethyl, propyl, butyl, pentyl, hexyl, heptyl, octyl, and isomers thereof. More preferably, where $R^1$ and/or $R^2$ are alkyl, they are independently selected from those alkyls having from 1 to 6 carbon 45 atoms, i.e., methyl, ethyl, propyl, butyl, pentyl, hexyl, and isomers thereof; most preferably, the alkyl group(s) have from 1 to 4 carbon atoms, i.e., methyl, ethyl, propyl, butyl, and isomers thereof. It is, however, most preferred that $R^1$ be hydrogen and that $R^2$ be hydrogen or a group of formula II.

In the present invention, of the compounds of formula I, the compounds taurolidine ($R^1$=H; $R^2$ =formula II) and taurultam ($R^1$=$R^2$=H) are particularly preferred. Taurolidine is bis-(1,1-dioxo-perhydroxy-1,2,4-thiadiazin-4-yl) methane.

These compounds are formaldehyde carriers, i.e., non-toxic derivatives containing formaldehyde in combination.

The mode of action of taurolidine has been shown to include the transfer of methylol groups to hydroxyl or amino groups present on the above toxins or on the mureine of the bacterial cell walls. In solution, taurolidine exists in equilibrium with taurultam and N-methylol taurultam, taurolidine being greatly predominant. Taurultam is itself in equilibrium with methylol taurinamide, the equilibrium being greatly in favor of taurultam. When the above methylol derivatives, methylol taurultam and methylol taurinamide, contact the toxins or bacteria, methylol groups are transferred. Methylol taurultam is thereby converted to taurultam, while methylol taurinamide is converted to taurine, a naturally occurring aminosulfonic acid that is extremely well tolerated in the human body. It will thus be appreciated that taurolidine and taurultam act in essentially the same way and produce the same final products.

Bacterial infections by gram-negative organisms are commonly accompanied by endotoxaemia, that is, by the reaction of the patient to the endotoxin liberated by the organisms.

Endotoxin is a complex lipopolysaccharide constituent of the O-somatic antigen and is loosely attached to the cell walls of gram-negative bacteria. Irrespective of the bacterial source, all endotoxins exhibit similar toxic properties-in contradistinction to the exotoxins of gram-positive bacteria, which exert a wide range of individual effects. In man, it can produce the syndrome of endotoxin shock when large numbers of gram-negative bacteria are lysed. This syndrome is encountered in about 30% of patients with gram-negative septicaemia. It is known that endotoxins can be inactivated by taurinamide derivatives.

Toxic proteins, such as, exotoxins, can similarly be inactivated and methylol transfer antibacterials can be administered to combat toxic proteins in the absence of lipopolysaccharide toxins. Toxins that may be concerned include the exotoxins of such gram-negative bacteria as *E. coli* and *Bacteroides fragilis*. It is known that intravenous administration to mice of 0.2 mL of a 20% solution of taurolidine in sterile 5% polyvinyl pyrrolidone can very significantly reduce the mortality rate on intraperitoneal administration of pathogenic strains of both *E. coli* and *B. fragilis*.

Other toxic proteins include venoms such as mellitin and fungal toxins such as amanitin and α-bungarotoxin, which have been shown to be substantially detoxified by taurolidine.

A particular advantage of taurolidine is its very low toxicity; it has been shown to be non-teratogenic in mice, the intraperitoneal $LD_{50}$ being on the order of 1.5 g/kg. As mentioned above, these compounds exhibit methylol transfer activity that results in the production of taurine, which is found naturally in the body and is particularly nontoxic. A further advantage of taurolidine is its stability in aqueous solution, enabling the solutions to be pre-packed and stored over relatively long periods.

These taurinamide derivatives will normally be administered as an aqueous solution by injection into the internal prosthetic device of the present invention. Such solutions may contain, in addition to a given taurinamide derivative, a solubilizing agent, such as, polyvinyl pyrrolidone (PVP), to help maintain the taurinamide derivative in solution and to contribute to the isotonicity of the solution. The concentration of the taurinamide derivatives in such solutions can range from greater than zero to about 2 wt %; concentrations in the range of from about 0.01 to about 1.5 wt % are preferred; and a concentration of about 1 wt % is most preferred. Higher concentrations than these would be useful, but in such cases, solubility becomes a problem.

Where PVP is incorporated into the solution, it will commonly be employed at a concentration in the range of from 4 to 7% by weight in order to achieve relatively high concentrations of the taurinamide derivatives, especially taurolidine, which have low water solubility. The molecular weight of the PVP should not be greater that about 30,000 and is preferably less than 10,000, e.g., between about 200 and 3500. Kollidone® 17, sold by BASF is especially suitable. Such PVP is fairly quickly absorbed and excreted through the kidneys.

The amount of solution of taurinamide derivative injected into the internal prosthetic device will normally be enough to fill it. Such systems typically have internal volumes in the range of from about 0.1 mL to about 10 mL; such quantities will, of course, vary with the length and diameter of any tubing used with the device, which, inter alia, can be a function of the size of the individual patient.

The concentration of the taurinamide derivative in such solutions is preferably in the range of from about 0.4 to about 5% by weight, depending, at the maximum, upon the solubility of the compound. Solutions of about 0.4 to about 2.0 weight % taurolidine, i.e., about 4 to about 20 grams per liter, are particularly preferred.

An example describing the preparation of a stock solution of taurolidine has appeared in several patents, for example, U.S. Pat. No. 4,337,251:

15 Liters of double distilled pyrogen free water is charged into a 25 liter glass vessel equipped with a stirrer and an intensive reflux device and heated to 50° C. with stirring. Taurolidine (400 g) is added followed by PVP (Kollidone 17; 1000 g). After dissolution, the solution is cooled and the pH is adjusted to 6.0 with a few drops of 0.1 N hydrochloric acid. The solution is then passed through an adsorption filter to remove microorganisms and pyrogens and through a sterilizing Millipore filter before being filled into 100 mL vials, which are finally autoclaved.

If desired, some or all of the PVP may be replaced by a parenterally acceptable polyol. This use for polyols has been disclosed in U.S. Pat. No. 5,210,083, the disclosure of which is incorporated herein by reference in its entirety. There, it is pointed out that this is advantageous because at higher concentrations of taurolidine, crystallization can occur, which can render the solution unusable.

In the case of bacteria and their endo- and exotoxins, it has been found that after the methylol transfer, as described above, there is a further irreversible step involving dehydration. Thus, in the case of bacterial endotoxins, which are lipopolysaccharides, it was found that an irreversible cross-linking reaction takes place that prevents the endotoxin from exerting its lethal effect. Similarly, in the case of bacterial exotoxins, which are proteins or polypeptides and do not contain lipopolysaccharide material of the kind found in the endotoxins, the detoxification reaction has been found to be irreversible. However, it is disclosed in U.S. Pat. No. 5,210,083 that the transfer of methylol groups by the mechanism set out above is reversible in the case of many hydroxyl or amino compounds, so that an equilibrium can be established that does not significantly interfere with the availability of taurolidine. Thus, polyols, such as, sugars and sugar alcohols, can also be used to maintain relatively high concentrations of taurolidine and/or taurultam in aqueous solution without significantly affecting their antibacterial and antitoxin activity. Preferred polyols include carbohydrates, e.g., hexoses, such as, glucose, fructose, and mixtures thereof; pentoses, such as, xylose; polysaccharides, such as, dextran or hydrolyzed starch; glycerol; and sugar alcohols, such as, sorbitol, mannitol, and xylitol. Glucose is most preferred.

The concentration of the polyol is typically in the range of from about 3 to about 40% by weight. In the case of glucose, the concentration is preferably in the range of from about 10 to about 30% by weight, more preferably about 20%.

Where such polyols are used, the concentration of taurolidine in the solution is preferably in the range of from about 0.5 to about 5%, more preferably in the range of from about 2 to about 3% by weight. The concentration of taurultam is preferably in the range of from about 1 to about 7.5%, more preferably in the range of from about 3 to about 5% by weight.

Since gram-negative organisms will frequently be present and since the bacteriostatic activity of the taurinamide derivatives is lower than that of many antibiotics, it may be advantageous to administer the compositions employed in the practice of the present invention in conjunction with a broad spectrum antibiotic substance, more especially, a substance strongly active against both gram-positive and gram-negative pathogens that, preferably, induces no or only delayed resistance, for example, a β-lactam antibiotic, such as, penicillin, ampicillin, or cephalosporin; a tetracycline antibiotic; a macrolide antibiotic, such as, erythromycin; a polypeptide antibiotic, such as, bacitracin or novobiocin; or, more preferably, an aminoglycoside antibiotic, such as, amikasin, butirosin, fortimycin, streptomycins, neomycin, linkomycins, such as, clindamycin and lincomycin, kanamycin, dideoxykanamycin B (DKP), lividomycin, netilmicin, ribostamycin, sagamycins, seldomycins and their epimers, sisomycin, sorbistin, tobramycin, vancomycin, gentamicin, and rifamycins, such as, rifampicin and rifamycin; and the like. Of these, gentamicin is preferred.

However, antibiotics are often contraindicated for use in surgical treatment, owing to their tendency to produce resistant strains, and, except in unusual cases, it is preferred that the taurinamide derivative be relied upon solely for the antibacterial action, since such derivatives do not produce resistant strains.

The composition employed in the practice of the present invention preferably also contains a pharmacologically acceptable carrier solution, such as, water, Ringer's solution, or saline. Additionally, the compositions of the present invention can also contain other dissolved additives that can favorably influence their physical and biochemical properties, for example, amino acids, sugar, common salt, fats, lipids, and the like.

When antimicrobial taurinamide derivatives are employed in the practice of the present invention, they are used in combination with a biologically acceptable acid or a biologically acceptable salt thereof. It is preferred that the acid be a carboxylic acid and more preferred that it be an anticoagulant as well. U.S. Pat. No. 5,077,281 teaches that taurolin compounds exhibit outstanding coagulation-inhibiting action in their own right and are especially suitable for use in medical conditions requiring dialysis and for vascular prostheses, either alone or in combination with other anti-coagulants such as coumarin or heparin. As pointed out in the patent, this is contrary to the teaching of "Taurolin", published by W. L. Bruckner and R. W. Pfirrmann, Verlag Urban und Schwarzenberg, Munich, 1985, which expressly states that taurolin does not influence blood coagulation and displays no anti-phlogistic action. It is the belief of the present inventors that the taurinamide derivatives employed in the practice of the present invention do exhibit a degree of anticoagulant activity, although to a lesser extent than is found with better known anticoagulants, such as heparin. Accordingly, it is beneficial to employ the taurinamide derivatives in combination with an anticoagulant, preferably one that is a biologically acceptable acid or salt thereof.

In accordance with the present invention, beneficial results are achieved when the antimicrobial taurinamide derivatives are combined with a biologically acceptable acid or biologically acceptable salt thereof so as to produce a pH for the ultimate composition that is no higher than 7, preferably in the range of from about 3.5 to about 6.5, more preferably in the range of from about 4.5 to about 6.5. Exemplary of such acids are acetic acid, dihydroacetic acid, benzoic acid, citric acid, sorbic acid, propionic acid, succinic acid, malic acid, fumaric acid, maleic acid, hydrochloric acid, malic acid, phosphoric acid, sulfurous acid, vanillic acid, tartaric acid, ascorbic acid, boric acid, lactic acid, ethylenediaminetetraacetic acid (EDTA), ethylene glycol-bis-{β-aminoethyl ether}-N,N,N',N'-tetraacetic acid, and diethylenetriamine pentaacetic acid, and the like, and biologically acceptable salts of the foregoing, such as, ammonium phosphate, potassium citrate, potassium metaphosphate, sodium acetate, sodium citrate, sodium lactate, sodium phosphate, and the like. A blood anticoagulating amount of an acid selected from the group consisting of citric acid, phosphoric acid, ethylenediaminetetraacetic acid (EDTA), ethylene glycol-bis-{β-aminoethyl ether}-N,N,N',N'-tetraacetic acid, and diethylenetriamine pentaacetic acid and biologically acceptable salts thereof is preferred. It is preferred that the acid employed in the practice of the present invention be an organic acid, especially one having at least one carboxyl group, particularly citric acid or EDTA. It is more preferred that the acid be citric acid and most preferred that it be used in combination with a citrate salt, e.g., sodium citrate.

Mermel, L. A. et al., in a talk entitled *Taurolidine Activity Against Vancomycin-Internediate Susceptibility Staphylococcus A ureus (VISA) and Methicillin-Resistant Staphylococcus Aureus (MRSA)* presented at the Interscience Conference on Antimicrobial Agents and Chemotherapy (1998), disclosed that taurolidine activity increases with decreasing pH in the range of from pH 7.0 to pH 5.0.

EDTA is a known anticoagulant that is used in blood collection tubes. It is also known to have the ability to form chelates with calcium. Since calcium is one factor that is known to have a role in the coagulation of blood, it is believed possible that at least part of EDTA's efficacy in anticoagulant activity may be brought about by this means. Sodium citrate is also believed to have anticoagulation properties by virtue of its ability to generate insoluble calcium citrate.

The foregoing acid anticoagulants can be used alone in the free acid state, but, more often will be employed with some or all of their carboxylic acid groups neutralized with an appropriate base or combined with a similar salt. Generally, it will be desirable to employ a cation that will form a salt that is soluble in aqueous solution, such as alkali metal ions, e.g., sodium or potassium. Zinc citrate may also be employed. Sodium or potassium salts are normally preferred, especially sodium, and the disodium salt of EDTA and sodium citrate are most preferred.

The acid and/or salt will be used in a concentration effective to bring about the desired anticoagulation effect and, at the same time, bring about, or help to bring about, an appropriate pH for biological use. Typically, the combined biocidal and anticoagulant composition of the present invention will have a pH in the range of from about 3.0 to about 7, preferably from about 3.5 to about 6.5 and, more preferably, from about 4.5 to about 6.5. The composition will normally be at a physiological pH. If necessary, the pH can be adjusted by additional acid or base, such as a mineral acid, for example hydrochloric acid, or, preferably, one that will not cause acidosis, such as, for example, acetic, malic, glutamic, aspartic, or lactic acid. Other methods for adjusting the pH, familiar to those of skill in the art, can also be employed. Where, as is preferred, trisodium citrate and citric acid are employed in the practice of the present invention, the trisodium citrate will typically be used in a concentration range of from about 5 to about 50 grams per liter. The citric acid will then be added in sufficient amount to bring the pH to the desired level.

Although the process of the present invention is primarily concerned with introducing the biocidal/anticoagulant compositions into internal prosthetic devices that are already in place, those skilled in the art will understand that contacting an artificial surface outside the body with these compositions can prevent the deposition of blood coagula on such surface after its implantation and aid in the elimination of sites for bacterial growth. Thus, the internal prosthetic device can be pre-treated, interiorly and/or exteriorly, by the compositions employed in the practice of the present invention to prevent the blockage due to blood coagula that present a favorable site for bacteria growth and thereby prevent the infection that may ensue. Such exterior treatments typically employ means for temporarily holding the compositions in place on the exterior of the device and then slowly permitting their release, e.g., porous materials, semi-permeable membranes, cationic or anionic species, as appropriate, and the like. The interior of the apparatus can be treated with a composition initially and then, after insertion, with repeated periodic flushing as referred to above.

Further, although the present invention is primarily and preferably directed to maintaining the patency and asepsis of implanted hemodialysis catheters, beneficial effects may also be obtained by its application to other, similar, internal prosthetic devices including, but not limited to, drains, catheters for peritoneal dialysis, central venous catheters, peripheral intervenous catheters, arterial catheters, Swan-Ganz catheters, umbilical catheters, percutaneous nontunneled silicone catheters, cuffed tunneled central venous catheters as well as with subcutaneous central venous ports.

Various features and aspects of the present invention are illustrated further in the examples that follow. While these examples are presented to show one skilled in the art how to operate within the scope of the invention, they are not intended in any way to serve as a limitation upon the scope of the invention.

EXAMPLE 1

A 0.5% solution of taurolidine in Ringer-lactate solution (Thomae, Biberach, Germany) was introduced into each of four polyethylene bottles having a 30 mL volume. Filling volumes were 5, 10, and 15 mL. One bottle was filled with 5 mL of the taurolidine solution and 2 mL ACD-A (Fresenius, Bad Homburg, Germany) solution. ACD-A solution is used for the conservation of whole blood and contains per liter: 22.0 grams of sodium citrate dihydrate, 7.3 grams of citric acid and 34.5 grams of glucose monohydrate.

Blood was collected at a slaughter house from a female pig directly from the slaughter wound into the containers that were then filled up to the 30 mL level. The containers were capped and gently moved to mix blood with the solution. The containers were inspected after 30 minutes. Blood in the containers containing only taurolidine was clotted, but the blood in the container containing the mixture of taurolidine and ACD-A was not clotted. Thus, it is concluded that the use of sodium citrate and citric acid anticoagulants in combination with taurolidine provides substantially enhanced anticoagulation properties in whole blood.

EXAMPLE 2

A subcutaneously implantable titanium port-system (hereinafter, DIALOCK™ port) of the type used in the practice of the present invention and described in U.S. Pat. No. 5,954,691 is used in this example. It is connected with two 12 French silastic catheters introduced with the tips into the right atrium. The valves of the port are opened by two special needles, as described above, allowing a blood flow of about 300 mL/min.

Ports were implanted by an experienced nephrologist in 10 female and 6 male patients whose mean age was 68±9 years, after their informed consent. Nine of the sixteen patients were diabetics. Patient inclusion criterion for the study was vessel exhaustion resulting in no blood access sites in the arms available for hemodialysis. Eight of the sixteen suffered from severe congestive heart failure and all had a high comorbidity. Nine of the patients started hemodialysis just after implantation, the others were on chronic hemodialysis and switched from catheter to the port system (four patient exchange by guidewire). No peri-operative complications occurred.

The preferred vessel was the right internal jugular vein, but the external jugular and subclavian veins were also used. The device has, thus far, been used for a total duration of 11.0 patient years. The ports were used for all planned IID sessions (n=1200).

In order to avoid intraluminal contamination of the device, an antimicrobial lock was applied between the sessions and removed before the next treatment. The aqueous antimicrobial biocidal lock comprised 13.3 grams/liter of taurolidine, 6.7 grams per liter of tri-sodium citrate, and approximately 3.3 grams per liter of citric acid. The citric acid was added to adjust the pH range to 4.75–5.25. By virtue of the citric acid and sodium citrate, clotting of the catheters was prevented and application of heparin was unnecessary.

During the period of the study, two episodes of bacteriaemia (*S. aureus*) were observed and successfully treated without loss of the device (0.5 infection per 1000 days).

EXAMPLE 3

In this example, the subcutaneously implantable DIALOCK port described in Example 2 was used.

Vessel exhaustion is an increasing problem in hemodialysis patients. In a prospective multi-center pilot trial starting June, 1998, 31 ports were implanted in 19 female and 12 male patients (mean age 66, min. 30, max. 81 years). In addition to the acceptance of the new device, the aim of the study was the avoidance of infection supported by the completely atoxic biocidal mixture (heparin-free biocidal lock containing taurolidine as an anti-infective substance and citric acid/sodium citrate for inhibition of coagulation) with excellent efficacy against any germs, even those with multi-resistance.

In ten participating centers, no port was lost since the start of the study (3,847 days of implantation). Despite high comorbidity, only two patients experienced blood-stream related infections (*S. aureus*). Total observed infection was 0.5 per 1000 days. Systemic antibiotic treatment was successful. Pre-existing catheter-related sepsis occurred in 5/31 patients; no relapse occurred in the patients using the subcutaneously implantable DIALOCK port.

Hospitalization was short and access was used just after implantation. The acceptance was high even in patients who switched from catheter to port (12/31). In 6/31 patients an exchange by guide-wire was possible. The usual placement technique was Seldinger applied by three nephrologists. The preferred vessel was the right internal jugular vein (18/31), but all other central veins were used.

The results of this study are shown in TABLE 1.

Compared to the disadvantages of catheters, the DIA-LOCK port system allows bathing and is very safe. Combined with the biocidal lock of the present invention, the risk of infection is low and allows a puncture technique similar to a graft. The lifetime of the device has yet to be established.

EXAMPLE 4

Comparative Example

In four separate facilities, two in the United States and two in Europe, A, B, C, and D, studies similar to those described above in Example 3 were carried out, except that the lock solution used was heparin or heparinized saline in concentrations in the range of from 2,000 to 10,000 international units per mL. In the studies in the United States, A and B, benzyl alcohol was also present as a standard preservative. The results of these comparative studies are shown in Table 1.

The filling solution comprises taurolidine, an antiseptic substance that has efficacy against fungi and multiresistant germs. Combined with citric acid and sodium citrate, clotting of the catheters is prohibited and application of heparin unnecessary. The mixture is absolutely atoxic and even can be injected intravenously without any harm. In order to avoid intraluminal contamination of the device and catheters, the anti-infective lock is applied between the sessions and removed before the next treatment by aspiration.

In a multi-center pilot trial starting in June, 1998, 28 ports were implanted by three experienced nephrologists after informed consent in 18 female and 10 male patients (mean age 68±9 yrs.) until January, 1999.

Eight dialysis centers participated in the study. The inclusion criterion was vessel exhaustion. 8/28 patients suffered from severe congestive heart failure, all had a high comorbidity. Start of hemodialysis (HD) just after implantation was in 13 patients, the other patients were on chronic HD, and 5 patients switched from catheter to port (exchange by guide wire). The preferred vessel was the right interior

TABLE 1

| Example | No of Patients | Time Pat. Yrs. | Explant for Cause (#s) | Infections | | | Fibrin/Thrombosis | |
|---|---|---|---|---|---|---|---|---|
| | | | | Number | Patients Affected (%) | Mean Interval[1] (Weeks) | Number | Mean Interval[2] (Weeks) |
| 3 | 31 | 11.0 | 0 | 2 | 7 | 286 | 0 | >500 |
| 4A | 8 | 8.0 | 1 | 6 | 50 | 70 | 2 | 208 |
| 4B | 4 | 4.2 | 2 | 10 | 75 | 22 | 4 | 54 |
| 4C | 7 | 6.1 | 2 | 6 | 43 | 53 | 4 | 79 |
| 4D | 4 | 3.4 | 0 | 0 | 0 | >176 | 0 | >176 |
| Total (Ex. 4) | 23 | 21.7 | 4 | 22 | 44 | 51 | 10 | 113 |

[1]Mean interval without infection.
[2]Mean interval without clotting.

EXAMPLE 5

An experiment was conducted to determine the minimum taurolidine/citrate biocidal lock acidity that will function well when in contact with human blood. Various biocidal lock acid concentrations were mixed 50/50 by weight with fresh whole human blood. The pH was experimentally varied from pH 3.0 to pH 7.0. At a biocidal lock acidity level of 4.0 and below, the resulting blood mixture becomes hard and concretionary after one hour of contact with the biocidal lock. This hardening was apparently due to the acid level of the biocidal lock and normal blood clotting, since the clot appears very dark in color and dry in nature, not normal in color or physical properties. When acidity of the biocidal lock was maintained above pH 5.0, no blood clotting occurred and blood color remained a healthy red color. Thus, the most preferred lower limit for the acidity of the taurolidine biocidal lock is about 5.0.

EXAMPLE 6

The risk of sepsis is the Achilles' heel of implanted venous catheters. The lock technique with antibiotics has not been wide-spread and cannot avoid fungal infections. In accordance with the present invention, an anti-infective biocidal lock has been developed for the application together with the DIALOCK port system. The subcutaneously implanted DIALOCK port is connected with two 12 French silastic catheters introduced with the tips into the right atrium. The valves of the port are opened by two special needles allowing a blood flow of up to 300 mL/min.

jugular vein (IJV, n=16), the others were: left IJV (n=4), both subclavian veins (n=8), and the exterior jugular vein in one patient. Total duration of the device use was 3,068 days, in nine patients more than six months. The puncture of the port was done without any special procedure after skin disinfection with alcohol.

Despite the fact that four patients had a septicaemic episode owing to catheter infections just before or during the time of implantation, no infection of the device occurred in the further course. Two episodes of blood-stream related infections with *S. aureus* were observed during the study period and successfully treated without loss of the device (0.65 infections/1000 days). The one patient developed a spondylitis and had an implanted catheter four months before the start of the study, the other patient with the positive blood culture had an immuno-suppressive therapy due to M. Crohn.

EXAMPLE 7

Clinical blood isolates of coagulase negative staphylococcus, *Candida albicans, Staphylococcus aureus, Enterococcus,* and *Pseudomonas aeruginosa* were inoculated into trypticase soy broth and allowed to incubate at 37° C. until the cultures were visibly turbid. Serial dilutions were made to obtain a final cell density of 10 colony forming units (cfu)/0.1 mL for *S. aureus, Enterococcus,* and *Pseudomonas aeruginosa*; 5 cfu/0.1 mL for Candida; 100 cfu/0.1 mL for coagulase negative staph. and Enterobacter. From the final dilution, 0.1 mL was instilled into each distal end of a DIALOCK port tube, and the DIALOCK port was incubated at room temperature overnight.

After incubation, a regular silicon catheter was placed on the distal end of both sides of each DIALOCK port. A solution of 5000 U/mL of heparin (with preservative) or 2% citrated taurolidine was instilled through the proximal end of the DIALOCK port to fill the DIALOCK port and catheter. The catheter was clamped and the DIALOCK port/catheter was incubated at 37° C. for 72 hours.

Following this incubation, both catheters were removed from each DIALOCK port and each was flushed with 0.1 mL of nutrient broth. A 0.1 mL aliquot of each flush was cultured on blood agar plates to determine the number of organisms remaining. The results are shown in Table 2.

TABLE 2

| Organism | Taurolidine | | Heparin | |
| --- | --- | --- | --- | --- |
| | Catheter | DIALOCK port | Catheter | DIALOCK port |
| Enterobacter | No growth | No growth | TNTC | TNTC |
| Coag. neg. staph. | No growth | No growth | No growth | TNTC |
| S. aureus | No growth | No growth | TNTC | TNTC |
| C. albicans | No growth* | No growth | 20 cfu | TNTC |
| Enterococcus | No growth | No growth | TNTC | TNTC |
| P. aeroginosa | No growth** | No growth | TNTC | TNTC |

TNTC = Too numerous to count.
*No growth of Candida albicans on the agar plate; however, there were a few colonies of a contaminant (coag neg staph & corynebacteria) likely from the external catheter surface.
**No growth of P. aeroginosa on the agar plate; however, there were two colonies of a contaminant likely from the external catheter surface.

In view of the many changes and modifications that can be made without departing from principles underlying the invention, reference should be made to the appended claims for an understanding of the scope of the protection afforded the invention.

What is claimed is:
1. An internal prosthetic device comprising:
   (a) means for providing a continuous flowpath, crossing a patient's skin, between an external-to-patient site and an internal-to-patient site;
   (b) means for blocking the flowpath; and
   (c) a biocidal lock comprising:
      (i) an anticoagulant; and
      (ii) a non-antibiotic biocide.
2. The device of claim 1 wherein said device is a catheter.
3. The device of claim 1 wherein said device is a port.
4. An internal prosthetic device access system comprising:
   (a) means for providing a continuous flowpath, crossing a patient's skin, between an external-to-patient site and an internal-to-patient site;
   (b) means for blocking the flowpath at a point under the patient's skin;
   (c) means for removing the flowpath portion crossing the patient's skin; and
   (d) a biocidal lock comprising:
      (i) an anticoagulant; and
      (ii) a non-antibiotic biocide.
5. The system of claim 4 wherein the system is a dialysis access system.
6. The system of claim 5 wherein the system is a hemodialysis access system.
7. A hemodialysis access system comprising:
   (a) means for providing a continuous flowpath, crossing a patient's skin, between an external-to-patient dialysis site and an internal blood vessel of the patient, the means including a flow conduit having no more than gentle changes in direction and whose internal surfaces are smooth and free of abrupt changes in flow area and define a flowpath sized for hemodialysis flow rates, and free of obstructions to provide low flow resistance and avoid any stagnation point;
   (b) means for blocking the flowpath at a point under the patient's skin;
   (c) means for removing the flowpath portion crossing the patient's skin; and
   (d) a biocidal lock comprising:
      (i) an anticoagulant; and
      (ii) a non-antibiotic biocide.
8. The system of claim 7 further comprising a flexible seal and wherein flowpath blockage is provided by the flexible seal, the flexible seal being entirely removable from the flowpath to establish a fully open configuration thereof free of obstructions and abrupt flow diameter or flow direction changes.
9. The system of claim 7 and further comprising means for activating and inactivating the flowpath forming portion of the system.
10. The system of claim 7 and further comprising means for increasing the available skin-crossing sites used in establishing the flowpath.
11. The system of claim 10 comprising a hollow needle which is insertable percutaneously by longitudinal pushing of it to a site where it defines a portion of the flowpath, and withdrawable by longitudinal pulling of the needle, and an implanted catheter comprising another portion of the flowpath and means for establishing a smooth continuous transition between the portions.
12. The system of claim 11 further comprising means for locking the inserted needle in place wherein the locking means is constructed and arranged to lock the needle upon longitudinal withdrawal movement accompanied by a lateral twisting movement.
13. The system of claim 12 further comprising an obturator within the hollow needle wherein the obturator has a pointed end arrangeable to protrude from a hollow needle ends.
14. The system of claim 7 wherein the anticoagulant is selected from the group consisting of di-ammonium hydrogen citrate, di-ammonium tartrate, N-(2-{bis(carboxymethyl)amino}ethyl)-N-(2-hydroxyethyl)glycin salt dihydrate, citric acid, citric acid disodium salt, citric acid monopotassium salt, citric acid monosodium salt, citric acid tripotassium salt, citric acid trisodium salt, ethylenediaminetetraacetic acid (EDTA), EDTA diammonium salt, EDTA dipotassium salt, EDTA disodium salt, EDTA tetrasodium salt, ethylenebis(oxyethylenenitrilo)tetraacetic acid (EGTA), EDTA trisodium salt, EDTA tripotassium salt, ethylene glycol-O,O'-bis(2-aminoethyl)-N,N,N',N'-tetraacetic acid, N-(2-hydroxyethyl)ethylenediamine-N,N',N'-triacetic acid trisodium salt, nitrilotriacetic acid, potassium sodium tartrate, potassium hydrogen D-tartrate, L-tartaric acid dipotassium salt, L-tartaric acid disodium salt, L-tartaric acid monosodium salt, tris(carboxymethyl) amine, heparin, warfarin, acetylsalicylic acid, ibuprofen, indomethacin, prostaglandins, sulfinpyrazone, streptokinase, urokinase, tissue plasminogen activator, coumarin, protamine sulfate, anti-thrombin III, coumadin, protein C/protein S, nicoumalone, phenprocoumon, hirudin, hirulog, glycosaminoglycans, and mixtures of the foregoing.
15. The system of claim 14 wherein the anticoagulant is a mixture of citric acid and trisodium citrate.

16. The system of claim 15 wherein the biocide is selected from the group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

17. The system of claim 15 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-aminohydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, and silver nitrate.

18. The system of claim 16 wherein the biocide is a taurinamide derivative of the formula:

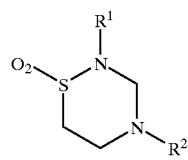

wherein $R^1$ is hydrogen or alkyl and $R^2$ is hydrogen, alkyl, or a group of the formula:

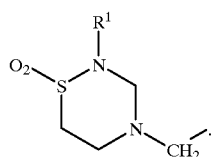

19. The system of claim 14 wherein the biocide is selected from the group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

20. The system of claim 19 wherein the biocide is a taurinamide derivative of the formula:

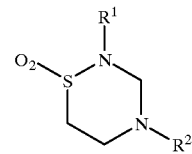

wherein $R^1$ is hydrogen or alkyl and $R^2$ is hydrogen, alkyl, or a group of the formula:

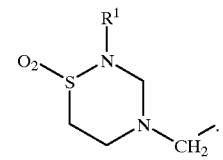

21. The system of claim 14 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-aminohydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, and silver nitrate.

22. The system of claim 7 wherein the biocide is selected from the group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

23. The system of claim 22 wherein the biocide is a taurinamide derivative of the formula:

wherein $R^1$ is hydrogen or alkyl and $R^2$ is hydrogen, alkyl, or a group of the formula:

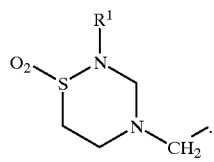

24. The system of claim 7 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-amino-hydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, and silver nitrate.

25. A hemodialysis access system for repeated access to a patient's vascular system, for hemodialysis repetitive blood exchange therapy, via a catheter that is subcutaneously implanted in the patient and has a distal end attached to a patient blood vessel and a proximal end near the patient's skin, the system comprising, in combination:

(a) a subcutaneously implantable access device having an entrance region, exit region and a passage therebetween provide for introduction of a needle thereby defining together with each other and the catheter a continuous streamlined flow path having no more than gentle changes in flow direction and being essentially free of stagnation points and constructed and arranged for blood flow through the flow path at a flow rate of at least 100 milliliters per minute;

(b) a needle for defining a continuous flowpath extension relative to the catheter and with a front part of the obturator emerging from a cannula front end and removable from the cannula, the cannula being constructed and arranged as a passage, when the obturator is removed, and means for communicating from the distal end of the cannula interior to an external patient site;

(c) the needle being constructed and arranged to puncture the patient's skin, to penetrate subcutaneous tissue and reach the entrance region of the implanted device and transit the passage of the latter to a point adjacent the exit region of the device and for withdrawal of the obturator of the needle means to thereby establish fluid communication between an external to the patient site and the catheter to provide a blood exchange path and flushing path from outside the patient to the patient's vascular system;

(d) means located within the device's passage at a site normally passed by needle insertion therein, for sealing the passage when the cannula/obturator is not in the passage and openable when contacted by the outer surface of the needle means, the seal and needle constructed and arranged so that the needle surface bears against the sealing material which is forced aside to an open position to permit the needle to transit the devices's passage, but without the point thereof contacting the sealing surfaces, the cannula being sufficiently rigid to hold the seal open when the obturator is withdrawn from the inserted cannula; and (e) a biocidal lock comprising:
  (i) an anticoagulant; and
  (ii) a non-antibiotic biocide.

26. The system of claim 25 wherein the passage comprises a region adjacent its exit for stopping the front end of the cannula of the inserted needle and forming a smooth walled flow path transition therewith.

27. The system of claim 25 wherein the anticoagulant is selected from the group consisting of di-ammonium hydrogen citrate, di-ammonium tartrate, N-(2-{bis (carboxymethyl)amino}ethyl)-N-(2-hydroxyethyl)glycin salt dihydrate, citric acid, citric acid disodium salt, citric acid monopotassium salt, citric acid monosodium salt, citric acid tripotassium salt, citric acid trisodium salt, ethylenediamine-tetraacetic acid (EDTA), EDTA diammonium salt, EDTA dipotassium salt, EDTA disodium salt, EDTA tetrasodium salt, ethylenebis(oxyethylenenitrilo)tetraacetic acid (EGTA), EDTA trisodium salt, EDTA tripotassium salt, ethylene glycol-O,O'-bis(2-aminoethyl)-N,N,N',N'-tetraacetic acid, N-(2-hydroxyethyl)ethylenediamine-N,N',N'-triacetic acid trisodium salt, nitrilotriacetic acid, potassium sodium tartrate, potassium hydrogen D-tartrate, L-tartaric acid dipotassium salt, L-tartaric acid disodium salt, L-tartaric acid monosodium salt, tris(carboxymethyl) amine, heparin, warfarin, acetylsalicylic acid, ibuprofen, indomethacin, prostaglandins, sulfinpyrazone, streptokinase, urokinase, tissue plasminogen activator, coumarin, protamine sulfate, anti-thrombin III, coumadin, protein C/protein S, nicoumalone, phenprocoumon, hirudin, hirulog, glycosaminoglycans, and mixtures of the foregoing.

28. The system of claim 27 wherein the anticoagulant is a mixture of citric acid and trisodium citrate.

29. The system of claim 28 wherein the biocide is selected from the group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

30. The system of claim 29 wherein the biocide is a taurinamide derivative of the formula:

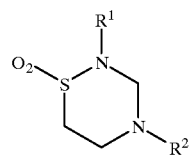

wherein $R^1$ is hydrogen or alkyl and $R^2$ is hydrogen, alkyl, or a group of the formula:

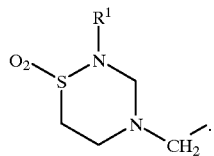

31. The system of claim 28 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-aminohydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, and silver nitrate.

32. The system of claim 27 wherein the biocide is selected from the group consisting of a taurinamide derivative, a phenol, quaternary ammonium, surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

33. The system of claim 27 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-aminohydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, and silver nitrates.

34. The system of claim 32 wherein the biocide is a taurinamide derivative of the formula:

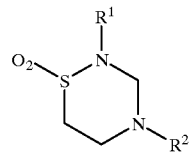

wherein $R^1$ is hydrogen or alkyl and $R^2$ is hydrogen, alkyl, or a group of the formula:

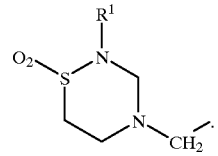

35. The system of claim 25 wherein the biocide is selected from the group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

36. The system of claim 35 wherein the biocide is a taurinamide derivative of the formula:

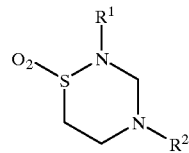

wherein $R^1$ is hydrogen or alkyl and $R^2$ is hydrogen, alkyl, or a group of the formula:

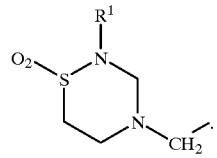

37. The system of claim 25 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-aminohydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4, 4'-trichloro-2'-hydroxydiphenol, thymol, chlorhexidine, benzalkonium chloride, cetylpyridinium chloride, silver sulfadiazine, and silver nitrate.

38. A hemodialysis access system for access to a human or animal patient's vascular system for high fluid flow rate exchange of blood between the vascular system and an external processing apparatus at a volumetric flow rate in excess of 100 mL/minute and having a decreased proclivity for effecting infection and blood coagulation, and comprising, in combination,
    (a) a needle assembly comprising a lumen defined by an interior surface and constructed and arranged for puncturing the skin of the patient and for carrying blood therethrough at a flow rate consistent with the high blood flow requirement of the blood exchange process;
    (b) a subcutaneously implantable access device permitting fluid connection to a vessel or space within a patient's body, the device comprising
        (i) a channel structure providing a flowpath having a straight or gently changing flow direction and having an interior surface and a distal end and a proximal end with reference to the patient's skin puncture site and constructed and arranged for insertion of the needle through the proximal end of the channel and withdrawal of the needle therefrom,
        (ii) a seal arranged within the channel and movable between first and second positions, where the seal, in the first position, with the needle not inserted through the seal, prevents fluids from passing the seal and, in the second position, with the needle inserted through the seal, allows fluids to pass through the needle and emerge substantially at the channel distal end, and where blood flowpath transitions between the needle interior surface and the channel interior surface are substantially continuous and smooth when the means for sealing is in the second position; and
the device further comprising structure for joining the channel distal end to a catheter that extends to an internal vessel of the patient's body, and wherein such joining is continuous and smooth along the interior surfaces of the channel and catheter; and
    (c) a biocidal lock comprising:
        (i) an anticoagulant; and
        (ii) a non-antibiotic biocide.

39. The the access system of claim 38 further comprising a catheter constructed and arranged for implantation between the device at a proximal cathether end and to or into a patient's blood vessel at a distal catheter end and means for attaching the device to the surrounding patient tissue.

40. The access system of claim 38 wherein the needle has a lumen and disposed along a first axis, the needle matingly corresponding to the inner surface and having a wall thickness of approximately 0.1 mm, and an obturator that is disposed within the needle along the first axis and matingly inserted into the lumen of the needle, the needle and obturator designed to provide an assembly with a pointed end constructed for opening the means for sealing, and means defining an access channel external to the patient communicating with the lumen of the needle, when it is inserted into the patient and through the means for sealing and wherein the access channel is disposed at an acute angle from the needle first axis.

41. The access system of claim 38 for high flow rate blood exchange between a human or animal patient with simultaneous flow in and out of the patient through separate paths, comprising at least one subcutaneously implantable access devise capable of being implanted in the patient just under the skin and having at least one passage therein, each with an entrance proximal to the skin and an exit distal therefrom, for accommodating one or more hollow needles, with interior lumens, percutaneously inserted therein, the transitions between the interior lumens of the needles and passage interiors of the device having gentle changes in flow direction and streamlined flowpaths, thereby permitting fluid connection to one or two blood vessels within a patient's body.

42. The access system of claim 41 further comprising means to secure the needles to each other and locking means to secure the needles within the device.

43. The system of claim 38 wherein the anticoagulant is selected from the group consisting of di-ammonium hydrogen citrate, di-ammonium tartrate, N-(2-{bis(carboxymethyl)amino}ethyl)-N-(2-hydroxyethyl)glycin salt dihydrate, citric acid, citric acid disodium salt, citric acid monopotassium salt, citric acid monosodium salt, citric acid tripotassium salt, citric acid trisodium salt, ethylenediaminetetraacetic acid (EDTA), EDTA diammonium salt, EDTA dipotassium salt, EDTA disodium salt, EDTA tetrasodium salt, ethylenebis(oxyethylenenitrilo)tetraacetic acid (EGTA), EDTA trisodium salt, EDTA tripotassium salt, ethylene glycol-O,O'-bis(2-aminoethyl)-N,N,N',N'-tetraacetic acid, N-(2-hydroxyethyl)ethylenediamine-N,N',N'-triacetic acid trisodium salt, nitrilotriacetic acid, potassium sodium tartrate, potassium hydrogen D-tartrate, L-tartaric acid dipotassium salt, L-tartaric acid disodium salt, L-tartaric acid monosodium salt, tris(carboxymethyl) amine, heparin, warfarin, acetylsalicylic acid, ibuprofen, indomethacin, prostaglandins, sulfinpyrazone, streptokinase, urokinase, tissue plasminogen activator, coumarin, protamine sulfate, anti-thrombin III, coumadin, protein C/protein S, nicoumalone, phenprocoumon, hirudin, hirulog, glycosaminoglycans, and mixtures of the foregoing.

44. The system of claim 43 wherein the anticoagulant is a mixture of citric acid and trisodium citrate.

45. The system of claim 44 wherein the biocide is selected from the group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

46. The system of claim 44 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5, 7-triazo 1-azoniaadamantane chloride, taurolidine, taurultam, EDTA, N(5-nitro-2-furfurylidene)-1-amino-hydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4, 4'-trichloro-2'-hydroxydiphenol, thymol, chlorhexidine, benzalkonium chloride, cetylpyridinium chloride, silver sulfadiazine, and silver nitrate.

47. The system of claim 45 wherein the biocide is a taurinamide derivative of the formula:

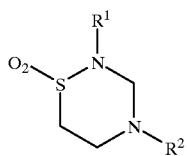

wherein R¹ is hydrogen or alkyl and R² is hydrogen, alkyl, or a group of the formula:

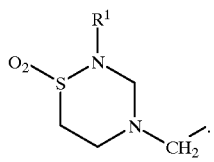

48. The system of claim 38 wherein the biocide is selected from the group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

49. The system of claim 48 wherein the biocide is a taurinamide derivative of the formula:

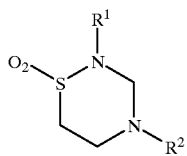

wherein R¹ is hydrogen or alkyl and R² is hydrogen, alkyl, or a group of the formula:

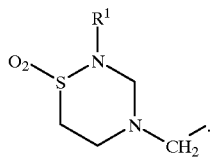

50. The system of claim 38 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-amino-hydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, and silver nitrate.

51. The system of claim 43 wherein the biocide is selected from the group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

52. The system of claim 51 wherein the biocide is a taurinamide derivative of the formula:

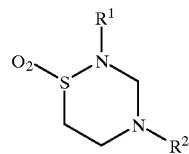

wherein R¹ is hydrogen or alkyl and R² is hydrogen, alkyl, or a group of the formula:

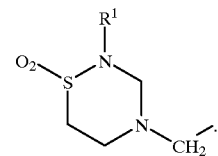

53. The system of claim 43 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-amino-hydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, and silver nitrate.

54. The system of claim 53 wherein the biocide is selected from the group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

55. A hemodialysis access system for use in a blood exchange therapy system, involving an extracorporeal blood processing apparatus operating at a flowrate of at least 100 milliliters per minute and being capable of allowing hundreds of such therapy cycles, the blood exchange therapy system comprising a catheter implanted in the patient and connected to a blood vessel of the patient at a distal end and having a proximal portion within the patient adjacent the patient's skin, and the access system comprising:
(a) means forming a continuous, streamlined flowpath running from outside the patient to the catheter, essentially free of surface discontinuities and flow stagnation sites and substantial pressure drops, the means comprising a channel structure providing a flowpath having no more than gentle changes in flow direction, and the means having two elements joining at an abutment with smooth transition at such abutment and all changes in flowpath cross-section being of a gradual nature, the means comprising:
 (i) a device implantable within the patient and having a passage therein;
 (ii) a needle that is insertable percutaneously into the patient and into the device passage to establish a portion of the flowpath and is withdrawable from the device and the patient; and
 (iii) a flexible seal in the device that automatically blocks the flowpath when the needle is not inserted and is entirely out of the flowpath when the needle is inserted and is not degraded by the repetitive therapy cycles of needles insertion, high volume blood exchange and needle withdrawal; and
(b) a biocidal lock comprising:
 (i) an anticoagulant; and
 (ii) a non-antibiotic biocide;
whereby a blood exchange therapy is maintainable with high resistance to blood clotting, infection, erythrocyte damage and platelet activation and with low pressure drop along the flowpath, consistent with the flow requirements of blood exchange therapy.

56. The system of claim 55 wherein the anticoagulant is selected from the group consisting of di-ammonium hydrogen citrate, di-ammonium tartrate, N-(2-{bis(carboxymethyl)amino}ethyl)-N-(2-hydroxyethyl)glycin salt dihydrate, citric acid, citric acid disodium salt, citric acid monopotassium salt, citric acid monosodium salt, citric acid tripotassium salt, citric acid trisodium salt, ethylenediaminetetraacetic acid (EDTA), EDTA diammonium salt, EDTA dipotassium salt, EDTA disodium salt, EDTA tetrasodium salt, ethylenebis(oxyethylenenitrilo)tetraacetic acid (EGTA), EDTA trisodium salt, EDTA tripotassium salt, ethylene glycol-O,O'-bis(2-aminoethyl)-N,N,N',N'-tetraacetic acid, N-(2-hydroxyethyl)ethylenediamine-N,N',N'-triacetic acid trisodium salt, nitrilotriacetic acid, potassium sodium tartrate, potassium hydrogen D-tartrate, L-tartaric acid dipotassium salt, L-tartaric acid disodium salt, L-tartaric acid monosodium salt, tris(carboxymethyl)amine, heparin, warfarin, acetylsalicylic acid, ibuprofen, indomethacin, prostaglandins, sulfinpyrazone, streptokinase, urokinase, tissue plasminogen activator, coumarin, protamine sulfate, anti-thrombin III, coumadin, protein C/protein S, nicoumalone, phenprocoumon, hirudin, hirulog, glycosaminoglycans, and mixtures of the foregoing.

57. The system of claim 56 wherein the anticoagulant is a mixture of citric acid and trisodium citrate.

58. The system of claim 57 wherein the biocide is selected from the group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

59. The system of claim 58 wherein the biocide is a taurinamide derivative of the formula:

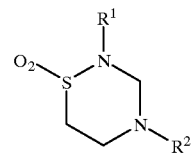

wherein $R^1$ is hydrogen or alkyl and $R^2$ is hydrogen, alkyl, or a group of the formula:

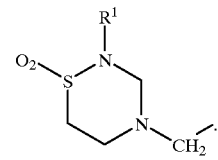

60. The system of claim 57 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-aminohydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, and silver nitrate.

61. The system of claim 54 wherein the biocide is a taurinamide derivative of the formula:

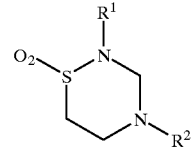

wherein $R^1$ is hydrogen or alkyl and $R^2$ is hydrogen, alkyl, or a group of the formula:

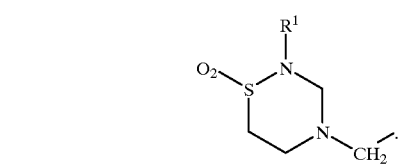

62. The system of claim 56 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-amino-hydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, and silver nitrate.

63. The system of claim 55 wherein the biocide is selected from the group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

64. The system of claim 63 wherein the biocide is a taurinamide derivative of the formula:

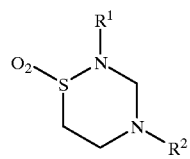

wherein $R^1$ is hydrogen or alkyl and $R^2$ is hydrogen, alkyl, or a group of the formula:

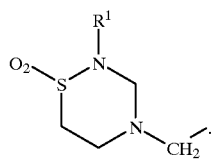

65. The system of claim 55 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-amino-hydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, and silver nitrate.

66. A hemodialysis access system for repeated access to a patient's distal vascular system in the course of long term fluid exchange therapy between the vascular system and a proximal blood processing site, via a catheter that is subcutaneously implanted in the patient and has a distal end coupled to a patient blood vessel and a proximal end, the system comprising, in combination, (a) a needle assembly comprising an elongated thin walled rigid cannula with ends proximal toward the blood processing site and distal toward the vascular system and an obturator constructed and arranged for insertion into the cannula and passing through its full length, and with a pointed distal end of the obturator emerging from a cannula distal end and removable from the cannula, the cannula being constructed and arranged, when the obturator is removed, for blood flow through the cannula interior at a high flow rate of at least 100 milliliters per minute, the cannula being constructed at its distal end for longitudinal flow of blood at such end to enter or exit the cannula and means for communicating from the back end portion of the cannula interior to an external blood processing site, (b) a subcutaneously implantable access device having entrance and exit regions and a passage therebetween which permits the cannula to enter the entrance end region and occupy a substantial passage length with a smooth transition between the cannula distal end and the device's exit region, the device being arrangeable subcutaneously with its exit region attached to the proximal catheter end and its entrance region accessible to the needle assembly through the patient's skin, the cannula interior and exit region thereby defining together a continuous streamlined flowpath having no more than gently changing flow direction and being essentially free of stagnation points or abrupt transitions and constructed and arranged for blood passage through the flow path defined thereby at a flow rate of at least 100 milliliters per minute, (c) the needle assembly being constructed and arranged to penetrate the patient's skin and subcutaneous tissue to reach the entrance region of the device and transit the passage of the latter to a point adjacent the exit region of the device and for withdrawal of the obturator to a point external of the patient's skin whereby the external blood processing site can be placed in fluid communication with the cannula and catheter to establish a blood exchange path, and a flushing path, from outside the patient to the patient's vascular system, (d) a seal located within the device's passage at a site normally passed by cannula/obturator insertion therein, and comprising means to close off the passage, when acted on by a biasing force, to produce a seal seating stress when the cannula/obturator is not in the passage and openable when contacted by the cannula/obturator constructed and arranged so that the external cannula/obturator surfaces bear against the means to force it aside to an open position, overcoming the bias force, to permit the cannula/obturator to transit the device's passage, but without the obturator distal point contacting the resilient sealing material, the cannula being sufficiently rigid to hold the seal open when the obturator is withdrawn from the inserted needle, and (e) a biocidal lock comprising:
(i) an anticoagulant; and
(ii) a non-antibiotic biocide.

67. The access system of claim 66 wherein the passage comprises a region adjacent its exit for docking with the distal end of the inserted cannula and forming a smooth walled flow path transition therewith.

68. The system of claim 66 wherein the anticoagulant is selected from the group consisting of di-ammonium hydrogen citrate, di-ammonium tartrate, N-(2-{bis(carboxymethyl)amino}ethyl)-N-(2-hydroxyethyl)glycin salt dihydrate, citric acid, citric acid disodium salt, citric acid monopotassium salt, citric acid monosodium salt, citric acid tripotassium salt, citric acid trisodium salt, ethylenediaminetetraacetic acid (EDTA), EDTA diammonium salt, EDTA dipotassium salt, EDTA disodium salt, EDTA tetrasodium salt, ethylenebis(oxyethylenenitrilo)tetraacetic acid (EGTA), EDTA trisodium salt, EDTA tripotassium salt, ethylene glycol-O,O'-bis(2-aminoethyl)-N,N,N',N'-tetraacetic acid, N-(2-hydroxyethyl)ethylenediamine-N,N', N'-triacetic acid trisodium salt, nitrilotriacetic acid, potassium sodium tartrate, potassium hydrogen D-tartrate, L-tartaric acid dipotassium salt, L-tartaric acid disodium salt, L-tartaric acid monosodium salt, tris(carboxymethyl)amine, heparin, warfarin, acetylsalicylic acid, ibuprofen, indomethacin, prostaglandins, sulfinpyrazone, streptokinase, urokinase, tissue plasminogen activator, coumarin, protamine sulfate, anti-thrombin III, coumadin, protein C/protein S, nicoumalone, phenprocoumon, hirudin, hirulog, glycosaminoglyeans, and mixtures of the foregoing.

69. The system of claim 68 wherein the anticoagulant is a mixture of citric acid and trisodium citrate.

70. The system of claim 69 wherein the biocide is selected from the group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

71. The system of claim 70 wherein the biocide is a taurinamide derivative of the formula:

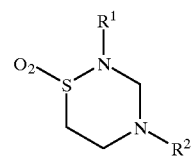

wherein $R^1$ is hydrogen or alkyl and $R^2$ is hydrogen, alkyl, or a group of the formula:

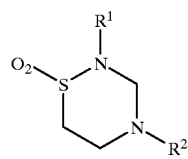

72. The system of claim 69 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5, 7-triazo 1-azoniaadamantane chloride, taurolidine, taurultam, EDTA, N(5-nitro-2-furfurylidene)-1-aminohydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4, 4'-trichloro-2'-hydroxydiphenol, thymol, chlorhexidine, benzalkonium chloride, cetylpyridinium chloride, silver sulfadiazine, and silver nitrate.

73. The system of claim 68 wherein the biocide is selected from the group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, arnidine, chelate and imidazoline biocides.

74. The system of claim 73 wherein the biocide is a taurinamide derivative of the formula:

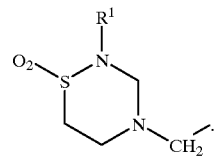

wherein $R^1$ is hydrogen or alkyl and $R^2$ is hydrogen, alkyl, or a group of the formula:

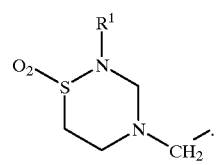

75. The system of claim 68 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-aminohydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, and silver nitrate.

76. The system of claim 66 wherein the biocide is selected from the group consisting of a taurinarnide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate and imidazoline biocides.

77. The system of claim 76 wherein the biocide is a taurinamide derivative of the formula:

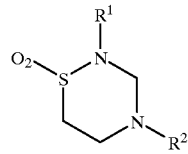

wherein $R^1$ is hydrogen or alkyl and $R^2$ is hydrogen, alkyl, or a group of the formula:

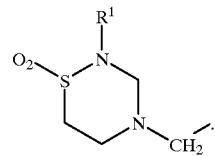

78. The system of claim 66 wherein the biocide is selected from the group consisting of acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-aminohydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, and silver nitrate.

\* \* \* \* \*